(12) United States Patent
Gross et al.

(10) Patent No.: US 8,995,955 B2
(45) Date of Patent: Mar. 31, 2015

(54) SYSTEMS, METHODS, AND MEDIA FOR LOGGING PHONE CALLS

(71) Applicants: Henry Gross, Long Island City, NY (US); Jennifer Gross, Long Island City, NY (US)

(72) Inventors: Henry Gross, Long Island City, NY (US); Jennifer Gross, Long Island City, NY (US)

(*) Notice: Subject to any disclaimer, the term of this patent is extended or adjusted under 35 U.S.C. 154(b) by 0 days.

(21) Appl. No.: 14/282,645

(22) Filed: May 20, 2014

(65) Prior Publication Data

US 2014/0342695 A1    Nov. 20, 2014

Related U.S. Application Data

(60) Provisional application No. 61/825,468, filed on May 20, 2013.

(51) Int. Cl.
| | |
|---|---|
| H04W 4/26 | (2009.01) |
| G06Q 50/24 | (2012.01) |
| G06F 19/00 | (2011.01) |
| H04M 3/22 | (2006.01) |
| H04M 15/00 | (2006.01) |
| H04M 3/42 | (2006.01) |
| H04W 4/16 | (2009.01) |

(52) U.S. Cl.
CPC ........... *G06F 19/322* (2013.01); *H04M 3/2218* (2013.01); *H04M 15/44* (2013.01); *G06F 19/328* (2013.01); *H04M 3/42221* (2013.01); *H04W 4/16* (2013.01)

USPC .............................................. 455/408; 705/3

(58) Field of Classification Search
CPC ..... H04W 12/00; H04W 12/02; H04W 12/04; H04W 12/06; H04W 12/08; H04W 12/10; H04W 12/12; H04W 4/24; H04W 4/26
USPC ....................... 705/2, 3, 50–54; 455/406–408
See application file for complete search history.

(56) References Cited

U.S. PATENT DOCUMENTS

| | | | |
|---|---|---|---|
| 2007/0005397 A1* | 1/2007 | Lee .................................. | 705/3 |
| 2009/0234780 A1* | 9/2009 | Drucker et al. ................ | 705/418 |
| 2010/0100463 A1* | 4/2010 | Molotsi et al. ................. | 705/32 |

* cited by examiner

*Primary Examiner* — Vladimir Magloire
*Assistant Examiner* — Erica Navar
(74) *Attorney, Agent, or Firm* — Byrne Poh LLP

(57) ABSTRACT

Methods, systems, and media for logging phone calls are provided. In some embodiments, methods for logging phone calls are provided, the methods comprise: causing a phone call to a client to be made; creating at least one note based on received user input; transmitting information about the phone call and the created note to the first server; causing the information and the note to be stored in association with the client by the first server; causing the information about the phone call and the note to be transmitted from the first server to a second server, wherein the information and the note are stored in an electronic medical record on the second server that is associated with the client; receiving an analysis of phone calls associated with the client over a period of time; and causing the analytical information to be presented based on the received analysis.

21 Claims, 48 Drawing Sheets

FIG. 36

SYSTEMS, METHODS, AND MEDIA FOR LOGGING PHONE CALLS

CROSS REFERENCE TO RELATED APPLICATIONS

This application claims the benefit of U.S. Provisional Patent Application No. 61/825,468, filed May 20, 2013, which is hereby incorporated by reference herein in its entirety.

TECHNICAL FIELD

The disclosed subject matter relates to systems, methods, and media for logging phone calls.

BACKGROUND

When making a phone call to a client and/or contact (e.g., a patient of a doctor, a student of a teacher, a client of an attorney, etc.), a user of a mobile device may want to make notes regarding the phone call and/or to track information about the phone call. For example, the user may want to take notes regarding a matter discussed during the phone call (e.g., a diagnosis, discussion about a case, discussion about a student in a class, etc.). As another example, the user (e.g., a doctor) may want to record the phone call and/or to store information about the phone call (e.g., notes about the phone call, duration of the phone call, etc.) in compliance with the Health Insurance Portability and Accountability Act (HIPAA) regulations. As yet another example, the user may want to store the duration of the phone call and/or other information about the phone call to charge the recipient of the phone call for the time spent on the phone call.

Accordingly, it is desirable to provide new systems, methods, and media for logging phone calls.

SUMMARY

Methods, systems, and media for logging phone calls are provided. In accordance with some embodiments of the disclosed subject matter, methods for logging phone calls are provided, the methods comprising: receiving a user request to make a phone call to a client; receiving, from a first server, contact information associated with the client; causing the phone call to be made based on the received contact information; receiving a user input of content relating to the phone call; creating at least one note based on the received user input; in response to determining that the phone call has been terminated, transmitting information about the phone call and the created note to the first server; causing the information about the phone call and the note to be stored in associated with the client by the first server; causing the information about the phone call and the note to be transmitted from the first server to a second server, wherein the information and the note are stored in an electronic medical record on the second server that is associated with the client; receiving a user request for analytical information relating to the client; receiving, from the first server, an analysis of a plurality of phone calls associated with the client over a period of time, wherein the analysis is based at least in part on a total duration of the plurality of phone calls during the period of time and a plurality of notes associated with the plurality of phone calls; and causing the analytical information to be presented based on the received analysis.

In accordance with some embodiments of the disclosed subject matter, systems for logging phone calls are provided, the systems comprising: a hardware processor that is configured to: receive a user request to make a phone call to a client; receive, from a first server, contact information associated with the client; cause the phone call to be made based on the received contact information; receive a user input of content relating to the phone call; create at least one note based on the received user input; in response to determining that the phone call has been terminated, transmit information about the phone call and the created note to the first server; cause the information about the phone call and the note to be stored in associated with the client by the first server; cause the information about the phone call and the note to be transmitted from the first server to a second server, wherein the information and the note are stored in an electronic medical record on the second server that is associated with the client; receive a user request for analytical information relating to the client; receive, from the first server, an analysis of a plurality of phone calls associated with the client over a period of time, wherein the analysis is based at least in part on a total duration of the plurality of phone calls during the period of time and a plurality of notes associated with the plurality of phone calls; and cause the analytical information to be presented based on the received analysis.

In accordance with some embodiments of the disclosed subject matter, non-transitory computer-readable media containing computer executable instructions that, when executed by a processor, cause the processor to perform a method for logging phone calls are provided, the method comprising: receiving a user request to make a phone call to a client; receiving, from a first server, contact information associated with the client; causing the phone call to be made based on the received contact information; receiving a user input of content relating to the phone call; creating at least one note based on the received user input; in response to determining that the phone call has been terminated, transmitting information about the phone call and the created note to the first server; causing the information about the phone call and the note to be stored in associated with the client by the first server; causing the information about the phone call and the note to be transmitted from the first server to a second server, wherein the information and the note are stored in an electronic medical record on the second server that is associated with the client; receiving a user request for analytical information relating to the client; receiving, from the first server, an analysis of a plurality of phone calls associated with the client over a period of time, wherein the analysis is based at least in part on a total duration of the plurality of phone calls during the period of time and a plurality of notes associated with the plurality of phone calls; and causing the analytical information to be presented based on the received analysis.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 36 shows an example of a user interface for presenting a call log and/or call history in accordance with some embodiments of the disclosed subject matter.

DETAILED DESCRIPTION

Figure 1:
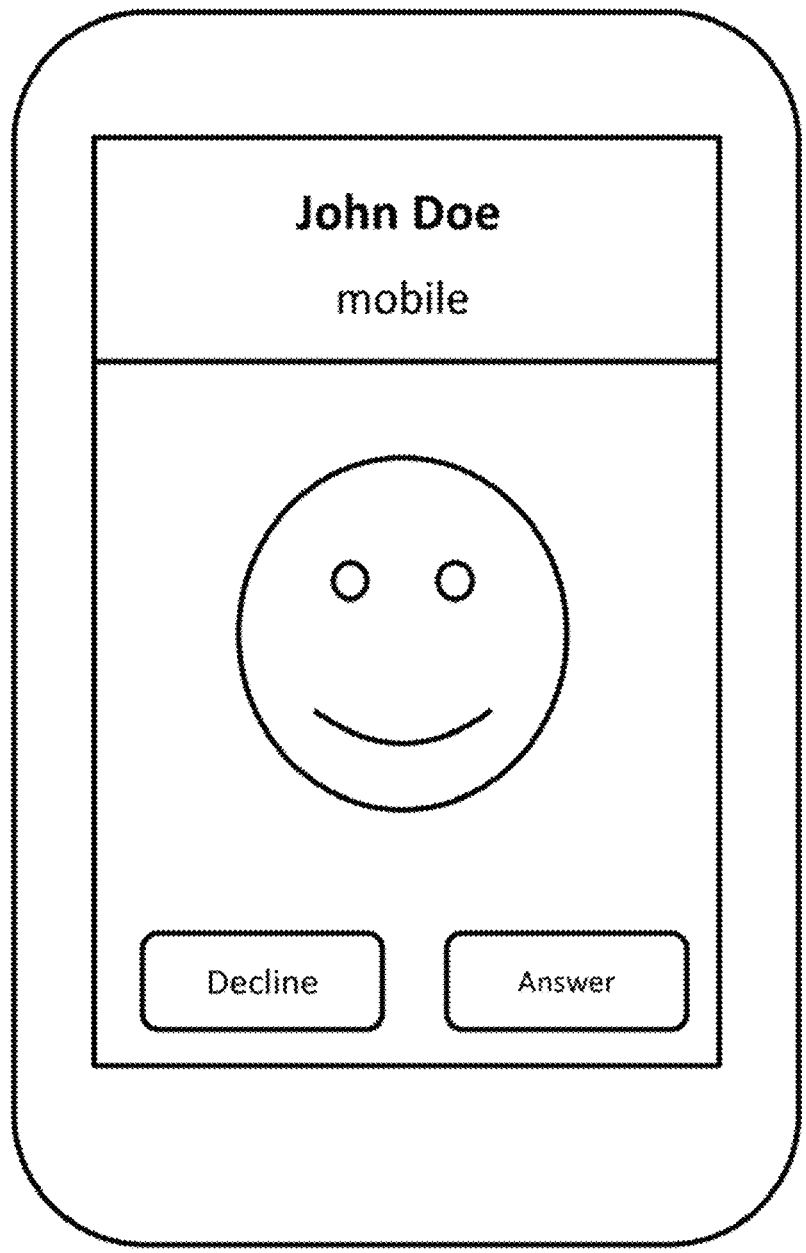
FIG. 1 shows an example of a user interface for starting a call in accordance with some embodiments of the disclosed subject matter.

In accordance with some embodiments, mechanisms for logging phone calls are provided. In some embodiments, these mechanisms can allow a user to make phone calls, record phone calls, schedule a reminder for follow-up calls, and store and synchronize contact information, information regarding communication with clients and/or contacts (e.g., dates, times, and/or durations of phone calls with contacts, dates and/or contents of emails with contacts, and/or any other suitable information), and/or one or more notes associated with a phone call. In some embodiments, the information can be synchronized and/or stored using an external device, for example, a server (e.g., a cloud suite, a remote storage device, and/or any other suitable server). In some embodiments, the information can be accessed and/or edited from any suitable user device, such as a mobile phone, a tablet computer, a desktop computer, a laptop computer, and/or any other suitable user device.

In some embodiments, data associated with a set of phone calls can be analyzed and/or accessed from any suitable user device. Examples of data can include: an average number of phone calls over a particular time period (e.g., an average number of phone calls to a particular contact and/or an average number of phone calls to a group of contacts); an average duration of phone calls over a particular time period (e.g., an average duration of phone calls to a particular contact and/or an average duration of phone calls to a group of contacts); a total number of phone calls (e.g., a total number of phone calls to a particular contact and/or a total number of phone calls to a group of contacts); and any notes and recordings associated with phone calls.

In some embodiments, the analyzed data can be presented in response to any suitable indication and/or signal. For example, in some embodiments, the analyzed data can be presented in response to a user request. As a more particular example, in some embodiments, the analyzed data can be presented in response to a request specifying that information related to phone calls with a particular contact are to be presented. As another example, in some embodiments, the analyzed data can be presented automatically at any suitable times (e.g., once per day, at 4 p.m., on Tuesdays, and/or at any other suitable times). In some embodiments, a user can specify criteria to be used in generating the analyzed data. For example, in some embodiments, the analyzed data can correspond to phone calls made to a particular set of contacts (e.g., contacts seen within the past week, contacts to be seen in the next week, all students in a class, and/or any other suitable set).

In some embodiments, data associated with any phone calls that are stored in a server can be exported and stored in any other suitable storage device. For example, in some embodiments, the data can be exported and saved on a user's computer, a second server and/or storage device that contains an Electronic Medical Record (EMR) associated with a particular patient, and/or any other suitable device.

It should be noted that, as referred to herein, a client and/or a contact can refer to any suitable recipient of a phone call. For example, a client and/or a contact can be a patient of a doctor, a client of a lawyer, a student of a teacher, a parent associated with a student of a teacher, and/or any other suitable recipient of a phone call.

Turning to FIGS. 1-25, mechanisms for tracking phone calls with clients, making notes about the phone calls, setting billable rates for the phone calls, and charging the clients at the billable rates is described.

In accordance with some embodiments, mechanisms for tracking billable time are provided. Generally speaking, these mechanisms can include a time tracking application that can allow users of the application to track time spent on a call with a client, make notes about the call, charge the client for the call at a suitable billing rate (e.g., a full billing rate, a discount billing rate, etc.), generate one or more invoices including information about one or more calls, etc.

In some embodiments, the application can allow a user to make a call (e.g., voice communications, video communications, multimedia communications, etc. using telephone services, voice over IP (VOIP) services, etc.) with a client using a suitable user device (e.g., such as a mobile phone, a tablet computer, a laptop computer, a desktop computer, etc.). Upon completion of the call, the application can collect suitable information about the call. For example, the application can obtain information about the start time and/or end time of the call, the duration of the call, information about the client, etc.

As another example, the application can prompt the user to provide suitable information about the call. In a more particular example, the application can prompt the user to identify a manner in which the client should be charged for the call (e.g., using one or more suitable interfaces). More particularly, for example, the user can instruct the application to charge the client at a full billing rate or a discount billing rate, disregard the call for billing purposes, etc. In another more particular example, the application can allow the user to create one or more notes relating to the call.

As yet another example, the application can obtain information about the client and manage a profile for the client. In a more particular example, the application can import a contact directory including information about one or more of the user's contacts from the user device. The application can then create and/or edit a profile for the client based on the information included in the contact directory and/or additional information relating to the client provided by the user. In another more particular example, the application can obtain a call history including information about one or more calls from the user device. The application can then create and/or edit a call log including information about the calls relating to the client (e.g., such as the duration of each call, the matters and/or cases relating to each call, etc.).

In some embodiments, upon gathering the information relating to the call and/or the client, the application can save the information in a suitable storage device (e.g., memory local to the user device, a server, etc.) and/or upload a part or all of the information to a server (e.g., such as a cloud suite). For example, the application can upload to the server the information relating to the client, the phone number, the date and/or time of the call, the duration of the call, the notes relating to the call, the billing rate, the manner in which the client should be charged for the call, the contact directory, the call history, etc.

In some embodiments, the application can access suitable data relating to one or more calls stored in the server (e.g., such as the information relating to one or more calls, etc.). In some embodiments, the application can extract the data from the server in a suitable manner (e.g., in the form of one or more comma-separated values (CSV) files).

In some embodiments, the application can provide information about one or more calls to suitable billing software (e.g., billing software integrated into the time tracking application, billing software implemented in a separate application, etc.). For example, the application can provide the billing software with the data extracted from the server. In a more particular example, the data can be provided to the billing software in the form of one or more CSV files.

In some embodiments, upon receiving the data about the calls, the application can cause one or more invoices to be generated in a suitable manner. For example, an invoice can be generated for each client to charge the client for billable time relating to one or more calls. In a more particular example, the invoice may include multiple items, each of which can correspond to a particular call relating to the client. More particularly, for example, each item of the invoice can include any suitable information about the particular call, such as the date and/or time of the conversation, the duration of the conversation, the billing rate applied to the conversation, etc.

These and other features for time tracking are described herein by way of the examples shown in FIGS. 1-25.

In some embodiments, the application can allow a user to make a call and automatically track billable time spent on the call. For example, an interface 100 of FIG. 1 can be presented to the user to allow the user to start a call. As shown, interface 100 can include any suitable information about the caller, such as the name of the caller, an image of the telephone caller, etc. In some embodiments, the user can select a "decline" button to decline the incoming call. Alternatively, the user can select an "answer" button to start a call.

Figure 2:
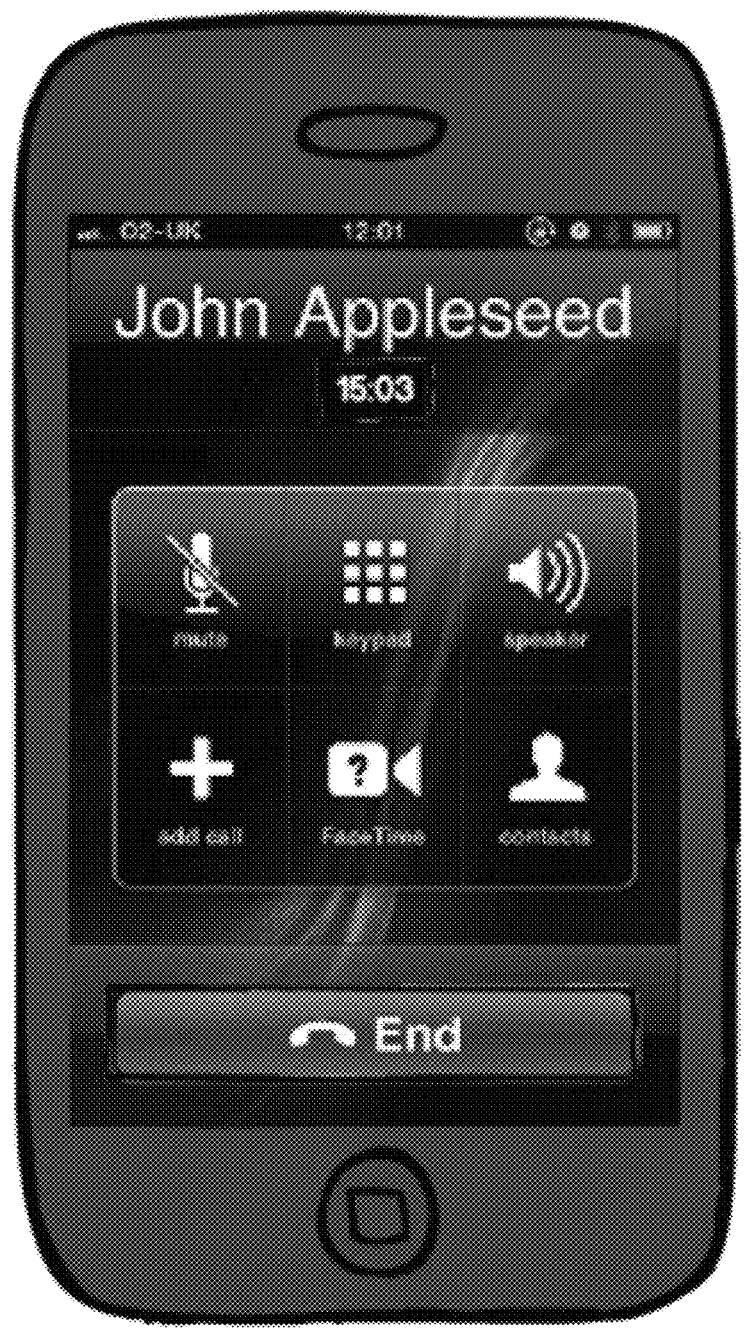
FIG. 2 shows an example of a user interface for viewing information about a call in accordance with some embodiments of the disclosed subject matter.

In some embodiments, an interface 200 as illustrated in FIG. 2 can be presented to the user to allow the user to view information about, and control the interface for, the call. In some embodiments, the user can select an "end" button to end the call.

Figure 3:
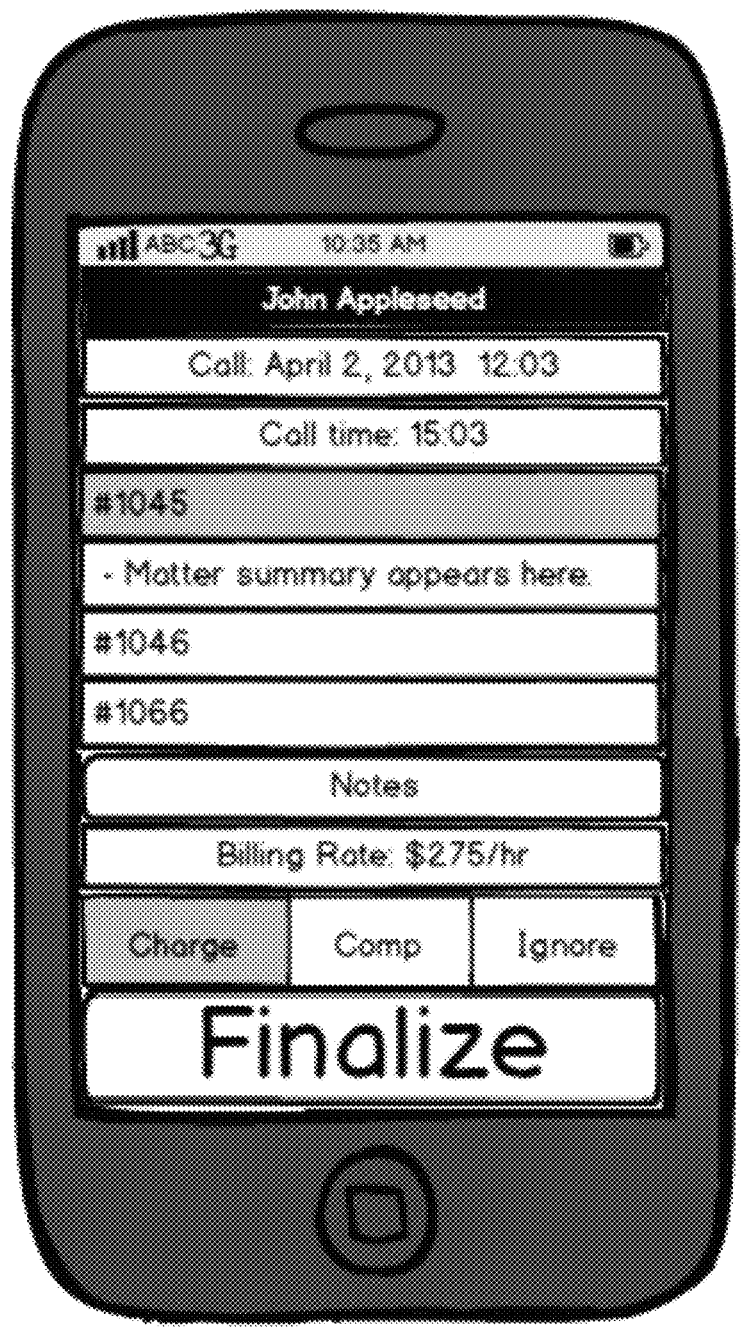
FIG. 3 shows an example of a user interface for editing information about a call in accordance with some embodiments of the disclosed subject matter.
Figure 4:
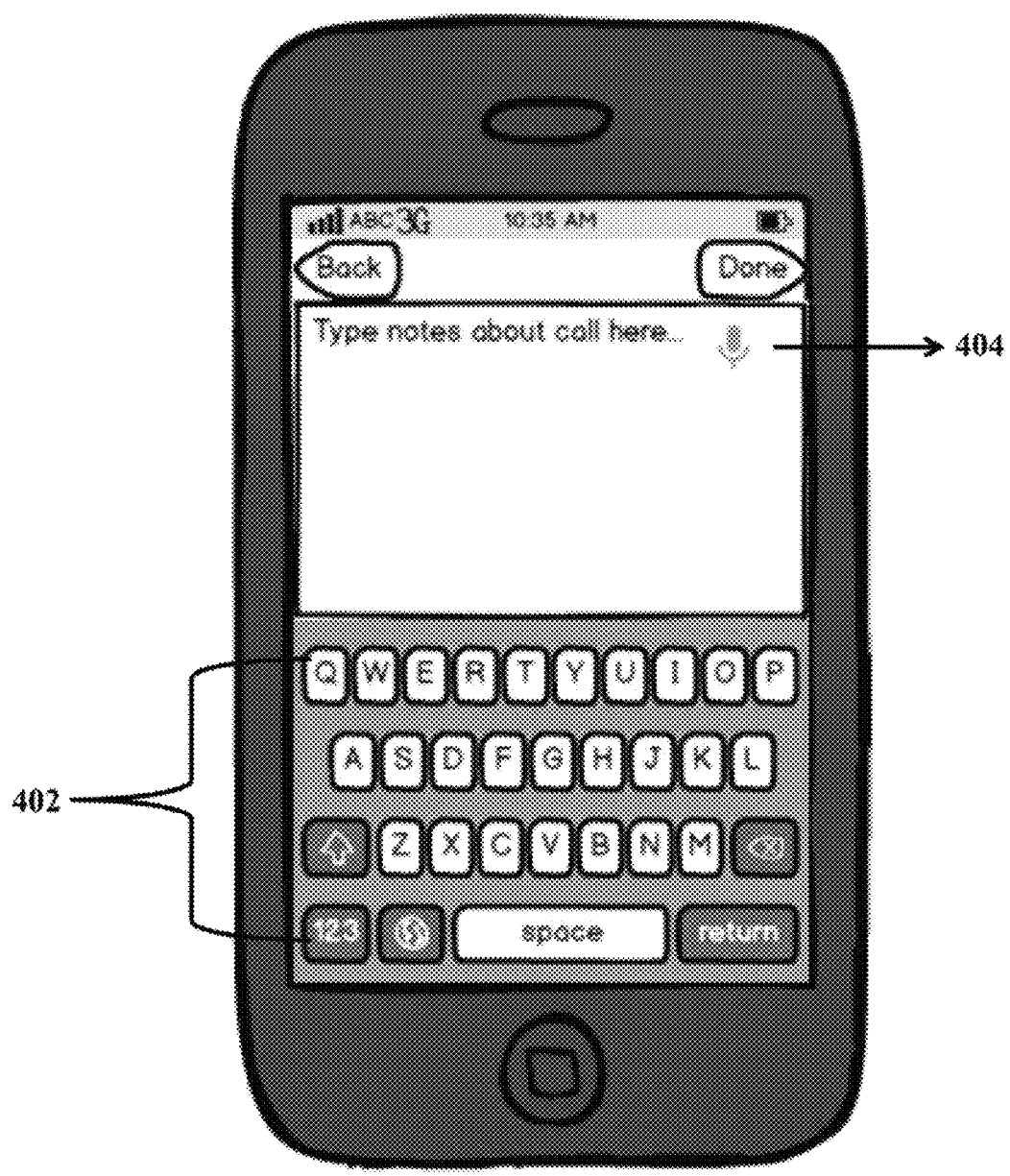
FIG. 4 shows an example of a user interface for viewing and/or editing one or more notes relating to a call in accordance with some embodiments of the disclosed subject matter.

In some embodiments, the application can allow the user to view and/or edit information about the call. For example, as illustrated in FIG. 3, an interface 300 can be presented to the user in response to the user selecting the "end" button in interface 200. Any suitable information about the call can be presented to the user in interface 300. For example, as shown, interface 300 can include information about the caller (e.g., such as the name of the caller, an image of the caller, etc.), the time and the date when the call is made, the duration of the call, the billing rate associated with the caller and/or the call, etc. As another example, interface 300 can include information about one or more matters and/or cases relating the caller, such as an identification number associated with each matter/case, a summary of each matter/case, etc.

In some embodiments, the application can allow the user to view and/or edit one or more notes relating to a call. For example, an interface 400 of FIG. 4 can be presented to the user in response to the user indicating a desire to view and/or edit the notes relating to a particular call (e.g., by selecting a "notes" button in interface 300). As shown, interface 400 can include one or more entry fields in which the notes relating to the call can be displayed and/or edited. The user can add and/or edit notes relating to the call in any suitable manner. For example, the user can enter the notes as texts using a keypad (e.g., such as a keypad 402 in interface 400). As another example, the user can record a voice memo by selecting and holding a recording button 404. As yet another example, the user can upload suitable images, documents, etc. that are associated with the call using interface 400. In some embodiments, the user can select a "done" button to save the notes and return back to interface 300. In some embodiments, the user can also select a "back" button to return to interface 300.

In some embodiments, the application can prompt the user to select an action to be taken with respect to a call for billing purposes. For example, as illustrated in FIG. 3, the user can select a "charge" button in interface 300 to charge the caller for the duration of the call at a full billing rate (e.g., the billing rate displayed in interface 300 of FIG. 3). As another example, interface 300 can allow the user to select a "comp" button to charge the caller for the duration of the call at a discount billing rate (e.g., by applying a 10% discount to the full billing rate, etc.). As yet another example, interface 300 can allow the user to select an "ignore" button to disregard the call for billing purposes.

Figure 5:
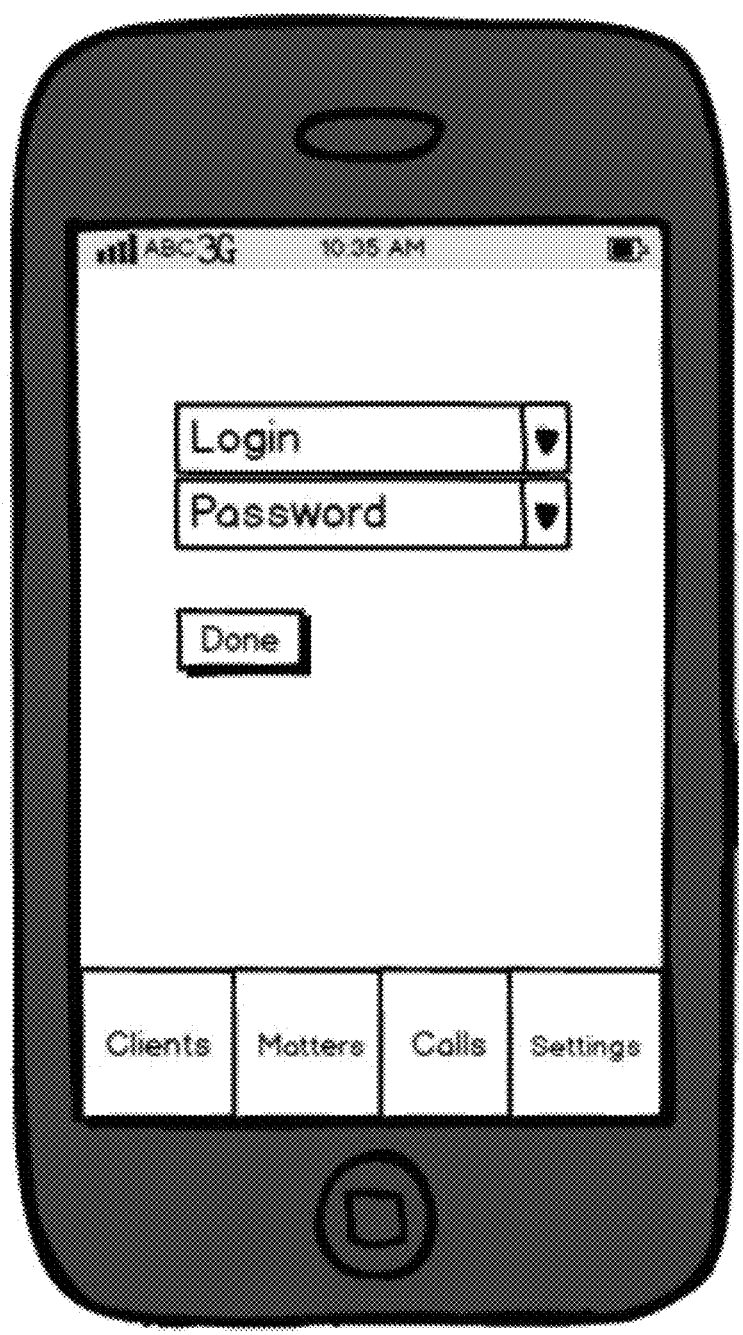
FIG. 5 shows an example of a user interface that can be presented to a user to allow the user to log into the user's time tracking account in accordance with some embodiments of the disclosed subject matter.

In some embodiments, upon viewing and/or editing the information presented in interface 300, the user can select a "finalize" button to save the information. In some embodiments, in response to the user selecting the "finalize" button, the application can prompt the user to log into the user's time tracking account using a suitable interface. For example, as illustrated in FIG. 5, an interface 500 can be presented to the user to allow the user to log into the user's time tracking account by entering suitable credentials (e.g., the user's user name, password, etc.).

In some embodiments, in response to the user logging into the user's time tracking account, the application can upload suitable information about one or more calls to a server (e.g., such as a cloud suite). For example, the application can upload to the server the information relating to the client, the phone number, the date and/or time of the call, the duration of the call, the notes relating to the call, the billing rate, the manner in which the client should be charged for the call, the contact directory, the call history, etc.

In some embodiments, the application can access suitable data relating to one or more calls stored in the server (e.g., such as the information relating to one or more calls, etc.). In some embodiments, the application can extract the data from the server in a suitable manner (e.g., in the form of one or more comma-separated values (CSV) files).

Figure 6:
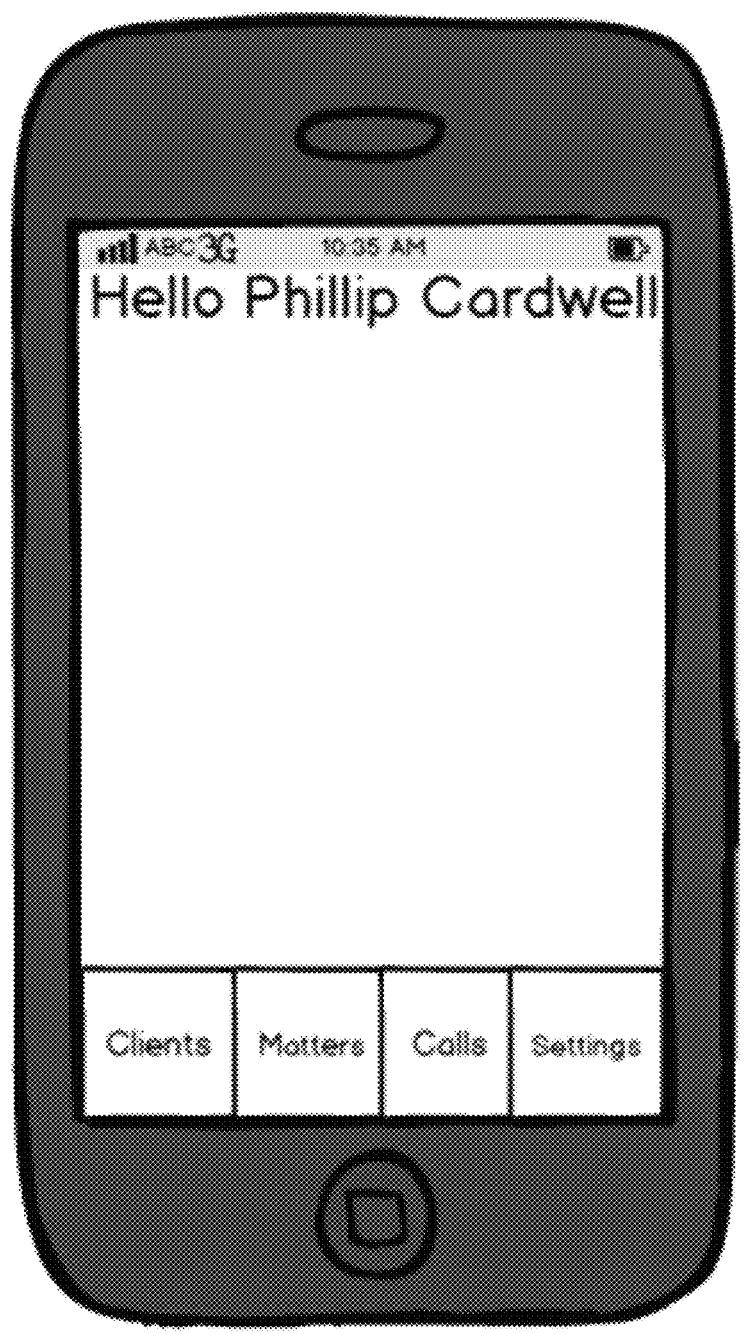
FIG. 6 shows an example of a user interface that can be presented to a user in response to the user logging into the user's account in accordance with some embodiments of the disclosed subject matter.

In some embodiments, in response to the user logging into the user's account, the application can present an interface 600 of FIG. 6 to the user. As shown, interface 600 can include a "clients" button, a "matters" button, and a "calls" button to allow the user to view and/or edit a directory of clients, a directory of matters, and a call log, respectively.

In some embodiments, the application can allow the user to view and/or edit information about matters/cases relating to one or more clients of the user. For example, an interface 700 can be presented to the user in response to the user indicating a desire to view and/or edit information relating to the matters/cases (e.g., by selecting the "matters" button of interface 600). Interface 700 can include any suitable information about the matters/cases such as an identification number associated with each matter/case, a summary of each matter/case, etc.

In some embodiments, the application can allow the user to view information relating to a particular matter/case using one or more suitable interfaces. For example, the user can select a particular matter/case (e.g., by selecting a matter displayed in interface 700) and view and/or edit information relating to the selected matter/case. In some embodiments, in response to the user selecting the particular matter, the application can present to the user an interface 800 of FIG. 8 to allow the user to view and/or edit information about the selected matter. Any suitable information about the selected matter/case can be presented using interface 800. For example, interface 800 can include the identification number of the matter, the name of the client with which the matter is associated, the billing rate for the matter, a summary of the matter, etc.

In some embodiments, the application can allow the user to set a billing rate associated with a particular matter/case and/or a particular client. For example, an interface 900 of FIG. 9 can be presented to the user in response to the user indicating a desire to view and/or set a billing rate (e.g., by selecting a "billing rate" button of interface 800). The billing rate can be set in any suitable manner. For example, the user can set a basis on which the client should be charged for the matter/case. In a more particular example, the user can select a "task" button in interface 900 to indicate that the client should be billed at the billing rate by task. In another more particular example, the user can select an "hr" button in interface 900 to indicate that the client should be charged at the billing rate based on the time that is spent on the matter/case. As another example, the user can set the amount of the billing rate in a suitable manner. In a more particular example, the user can enter the billing rate in a text field using the user device (e.g., using a keypad, an interface, a voice command, etc.). In another more particular example, the user can scroll through the numbers displayed on interface 900 to set a suitable billing rate. In some embodiments, after setting the billing rate, the user can select an "apply rate" button of interface 900 to save the billing rate and apply the billing rate to the matter/case and/or the client. In some embodiments, in response to the user selecting the "apply rate" button of interface 900, interface 800 of FIG. 8 can be presented to the user.

In some embodiments, the application can allow the user to view and/or edit a description of a particular matter/case. For example, an interface 1000 can be presented to the user in response to the user indicating a desire to view and/or edit a description of a particular matter/case (e.g., by selecting a "view entire matter" button of interface 800). The description can be edited in any suitable manner. For example, interface 1000 can include one or more entry fields in which the user can enter one or more text descriptions to be associated with the matter/case. As another example, the user can record one or more voice memos to be associated with the matter/case using interface 1000.

Figure 11:
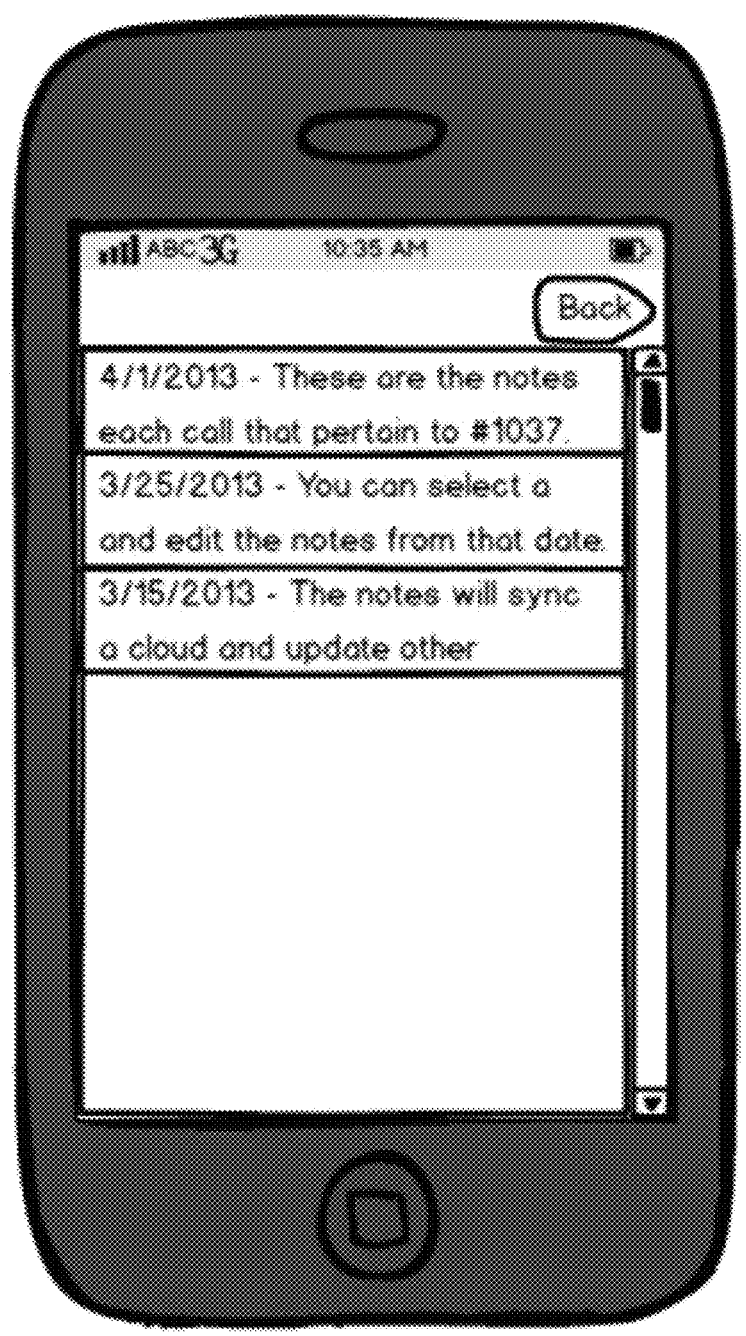
FIG. 11 shows an example of a user interface for viewing and/or editing one or more notes relating to a particular matter in accordance with some embodiments of the disclosed subject matter.

In some embodiments, the application can allow the user to view and/or edit one or more notes relating to a particular matter. For example, as illustrated in FIG. 11, an interface 1100 can be presented to the user in response to the user indicating a desire to view and/or edit the notes relating to the particular matter (e.g., selecting a "view matter notes" button in interface 800 of FIG. 8). Any suitable information can be included in the notes relating to the matter. For example, each of the notes can include the identification number of the matter/case, the date and duration of each call relating to the matter/case, a summary of each call relating to the matter/case, etc. In some embodiments, the application can allow the user to edit a particular note presented in interface 1100. For example, in response to the user selecting a particular note presented in interface 1100, the application can present one or more suitable interfaces to allow the user to edit the selected note. In a more particular example, interface 400 of FIG. 4 can be presented to the user in response to allow the user to edit the selected note.

Figure 12:
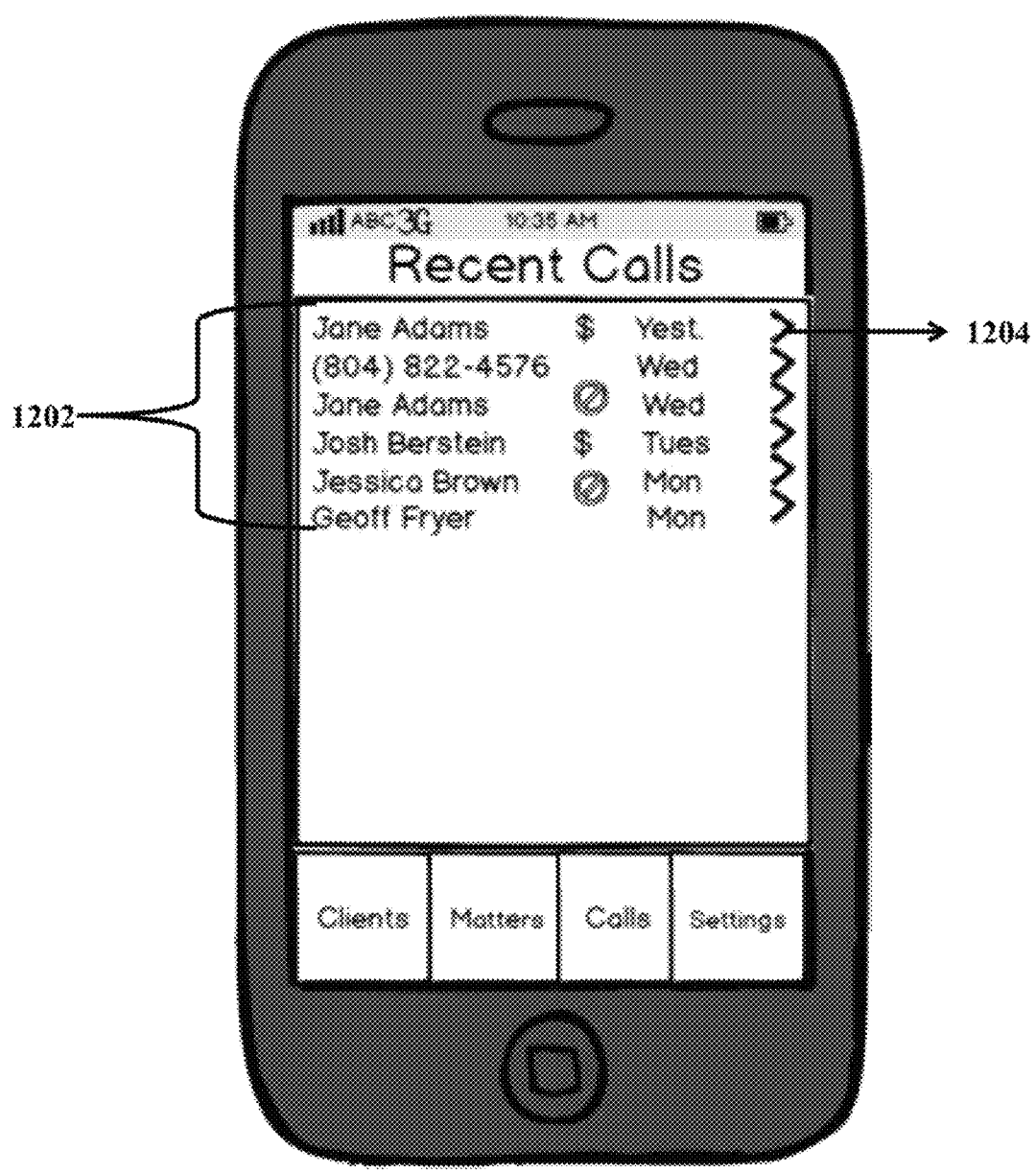
FIG. 12 shows an example of a user interface that can be presented to a user to allow the user to view information about phone calls relating to the user's time tracking account in accordance with some embodiments of the disclosed subject matter.
Figure 13:
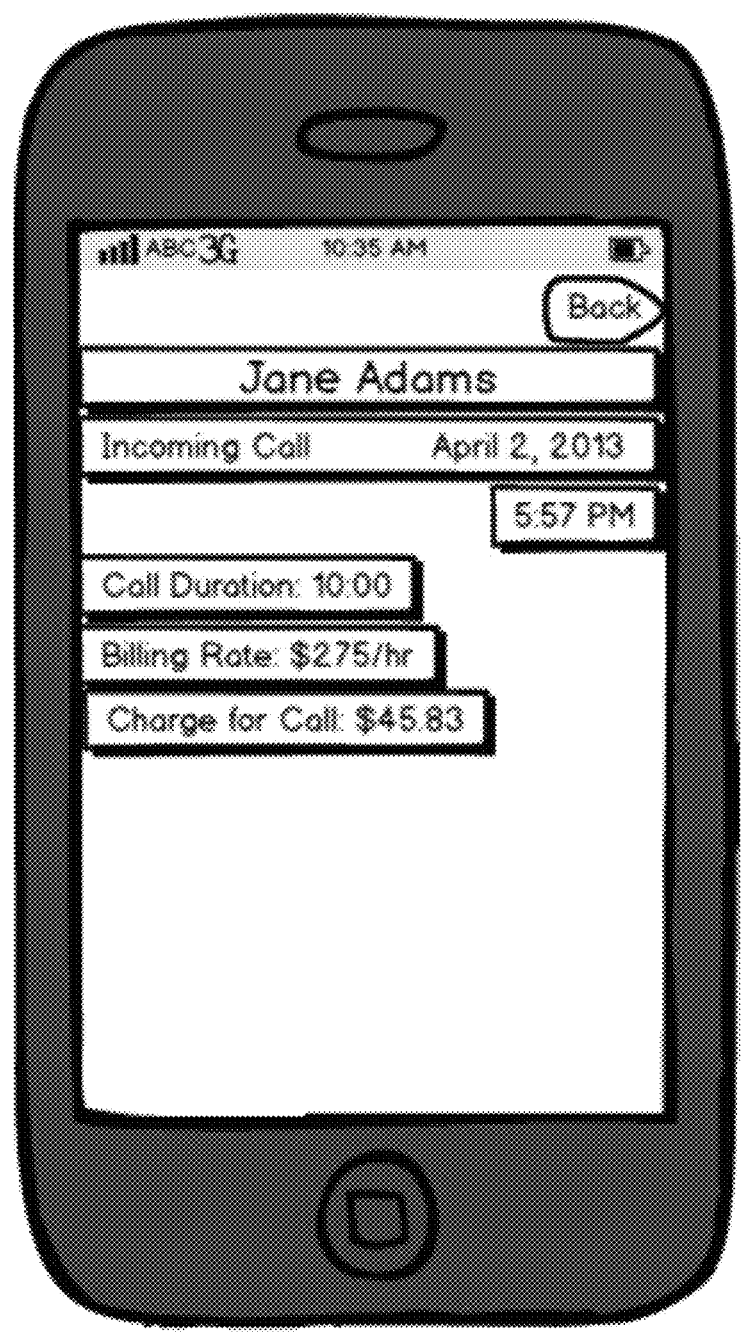
FIG. 13 shows an example of a user interface that can be presented to a user to allow the user to view and/or edit information relating to an entry of a call log in accordance with some embodiments of the disclosed subject matter.

In some embodiments, the application can allow the user to view information relating to one or more calls. For example, as illustrated in FIG. 12, an interface 1200 can be presented to the user in response to the user indicating a desire to view and/or edit information about the calls relating to the user's time tracking account (e.g., by selecting a "calls" button in interface 600). Any suitable information can be presented in interface 1200. For example, interface 1200 can include a call log 1202 including one or more entries. In some embodiments, each entry of the call log can include suitable information relating to a particular call, such as the name of the caller and/or callee, the phone number of the caller and/or callee, the time of the call, the manner in which the call should be charged (e.g., charging the client at a full billing rate, charging the client at a discount billing rate, disregarding the call for billing purposes, etc.), etc.

In some embodiments, the application can allow the user to view and/or edit information relating to a particular call. For example, the application can prompt the user to select a particular call from a call log and allow the user to view information relating to the selected call. In a more particular example, in response to the user selecting an entry of call log 1202 of FIG. 12 (e.g., by selecting a button 1204 corresponding to the entry), an interface 1300 of FIG. 13 can be presented to the user to allow the user to view and/or edit the information about the selected entry. Interface 1300 can include any suitable information about the selected call, such as the name of the caller and/or callee, a description of the call (e.g., an incoming call, an outgoing call, etc.), the date and time of the call, the duration of the call, the billing rate applied to the call, one or more charges relating to the call, etc.

Figure 7:
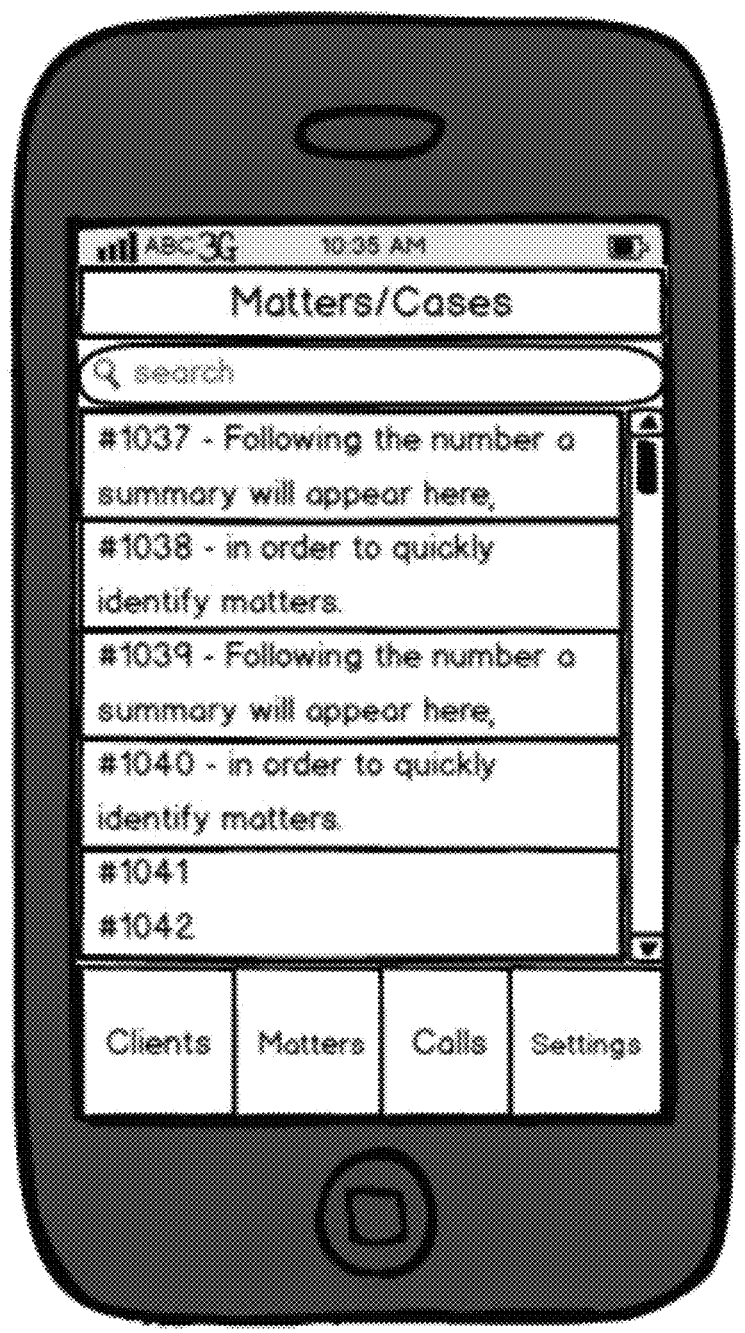
FIG. 7 shows an example of a user interface for viewing and/or editing information about matters/cases relating to one or more clients in accordance with some embodiments of the disclosed subject matter.
Figure 8:
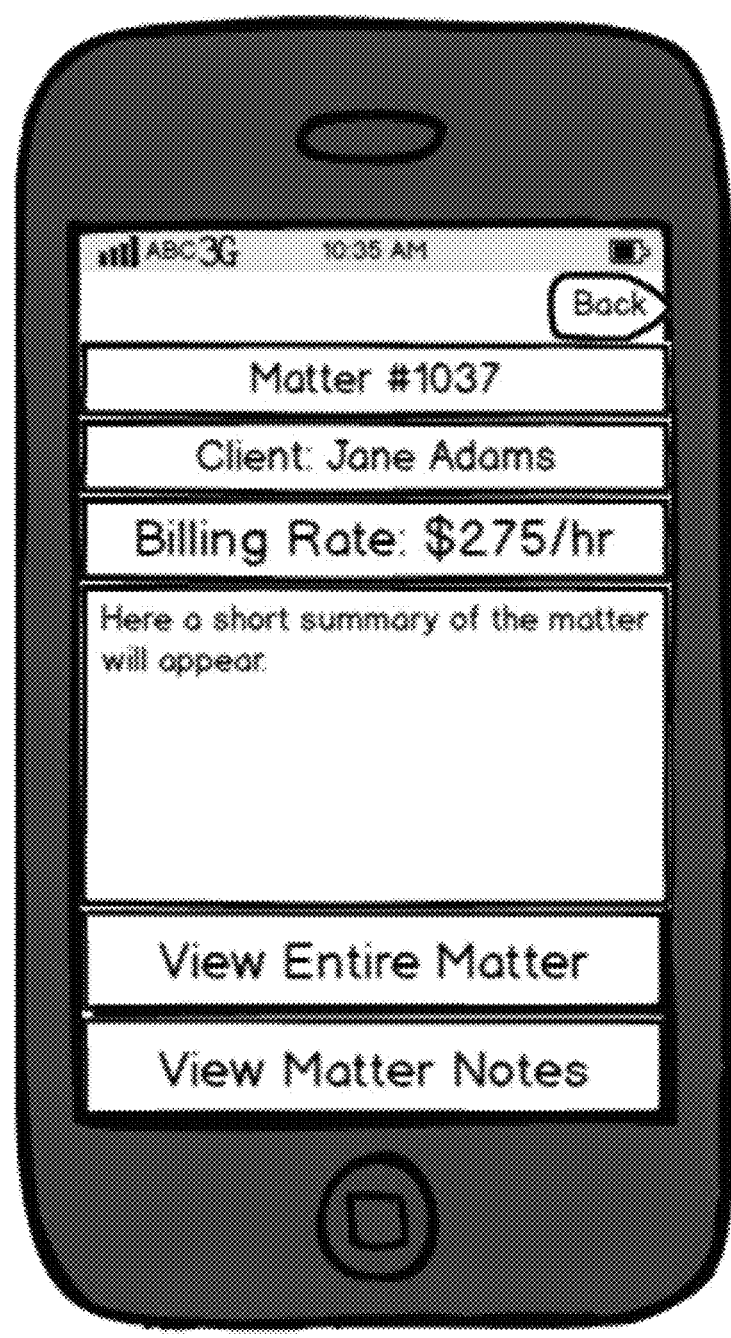
FIG. 8 shows an example of a user interface for viewing and/or editing information about a selected matter in accordance with some embodiments of the disclosed subject matter.
Figure 9:
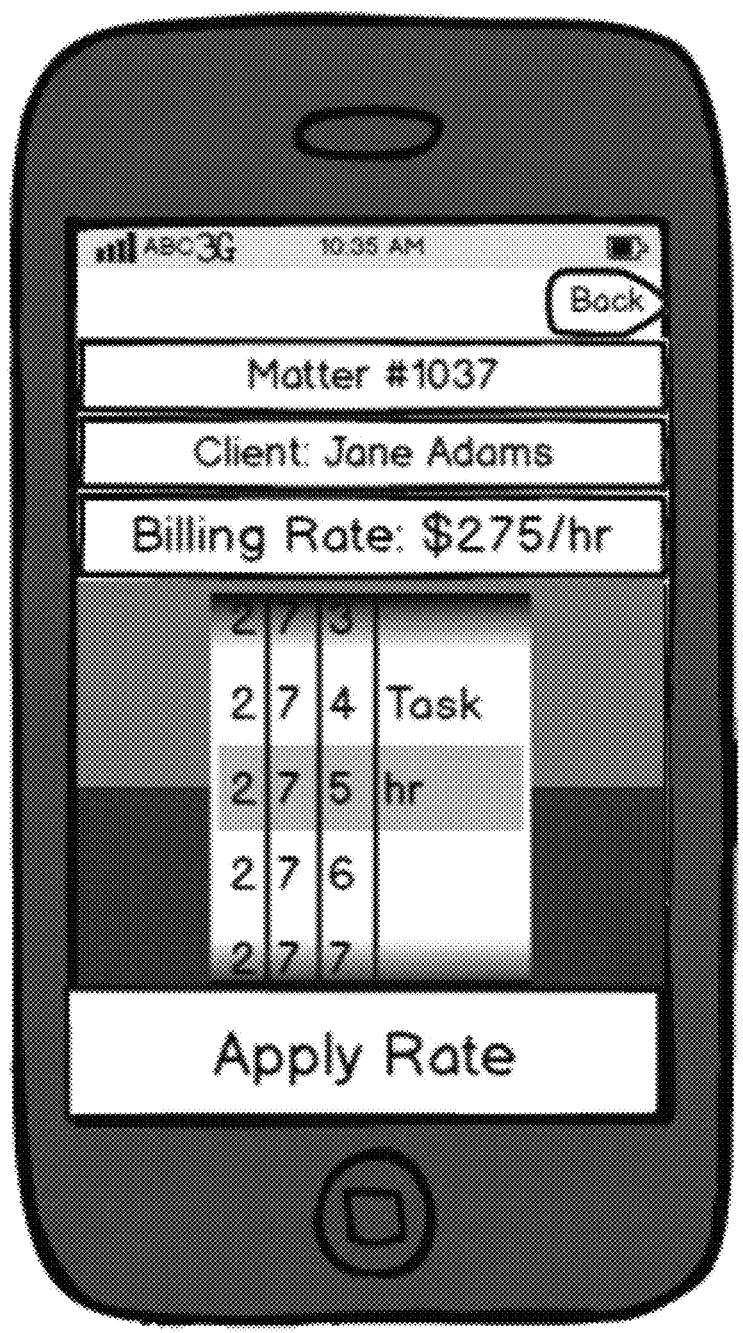
FIG. 9 shows an example of a user interface for setting a billing rate associated with a particular matter/case and/or a particular client in accordance with some embodiments of the disclosed subject matter.
Figure 10:
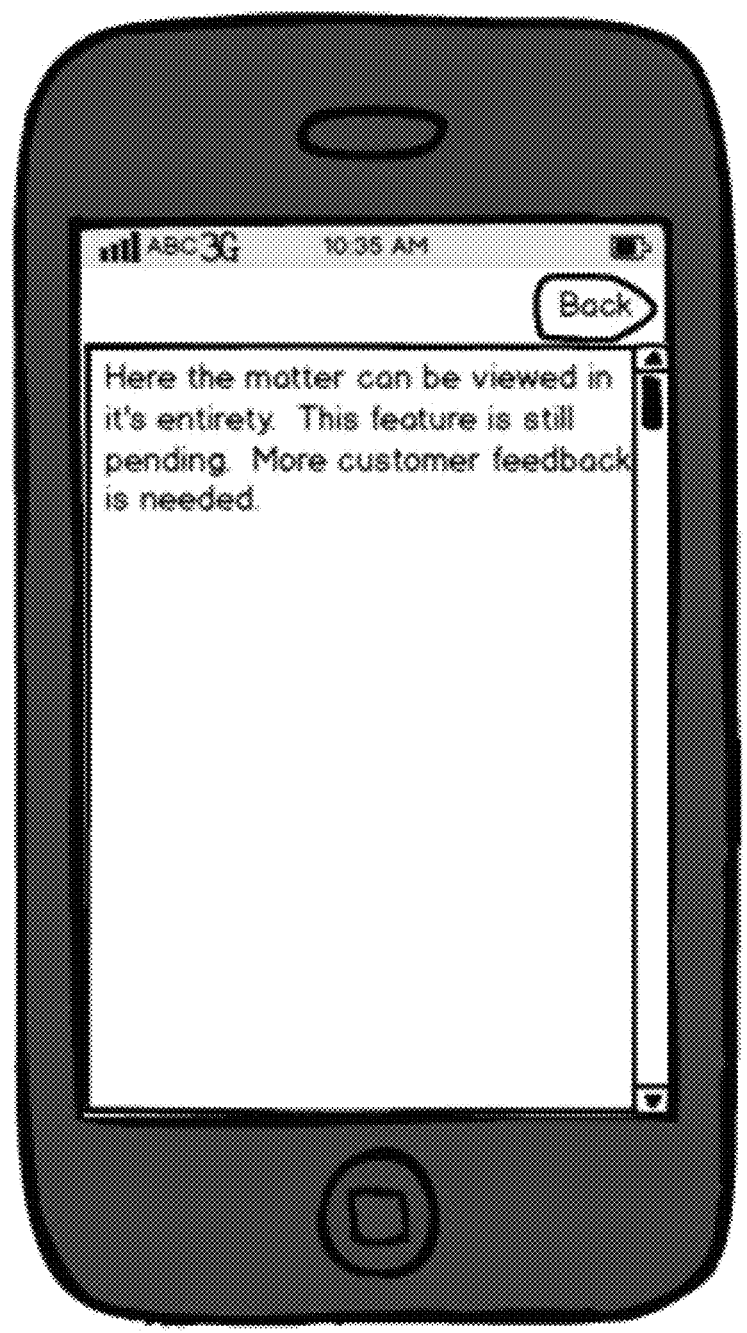
FIG. 10 shows an example of a user interface for viewing and/or editing a description of a particular matter/case in accordance with some embodiments of the disclosed subject matter.

In some embodiments, the application can allow the user to view and/or edit a directory of the user's clients and/or contacts. For example, an interface 1400 of FIG. 14 can be presented to the user in response to the user indicating a desire to view and/or edit a directory of clients and/or contacts (e.g., by selecting a "clients" button as illustrated in FIGS. 6, 7, and 12). As shown, interface 1400 can include a contact directory 1402. In some embodiments, contact directory 1402 can be imported from the user's contact directory stored in the user's user device. Contact directory 1402 can include any suitable information about the user's contacts, such as the name of each contact, whether each contact is a client of the user (e.g., using an icon 1404 to identify a client contact), etc.

In some embodiments, the application can allow the user to add a new contact to a contact directory. For example, in response to the user indicating a desire to add a new contact the contact directory (e.g., by selecting an add button 1406 in interface 1400), the application can cause an interface 1500 of FIG. 15 to be presented to the user. As shown, interface 1500 can include one or more text entry fields that can allow the user to enter any suitable information about the new contact, such as the name, phone numbers, email addresses, etc. of the new contact. In some embodiments, the user can also upload one or more photos to be associated with the new contact using interface 1500.

In some embodiments, the application can allow the user to designate a contact as a client contact and create a profile for the client contact. For example, the user can select a particular contact from a contact directory (e.g., contact director 1402 of FIG. 14) and create a client profile for the selected contact. In some embodiments, in response to the user selecting the particular contact, the application can present interface 1600 of FIG. 16 to the user. As shown, the name of the selected contact can be identified on button 1602. In some embodiments, the user can cancel the selection by selecting a "clear" button 1604 of interface 1600.

Figure 14:
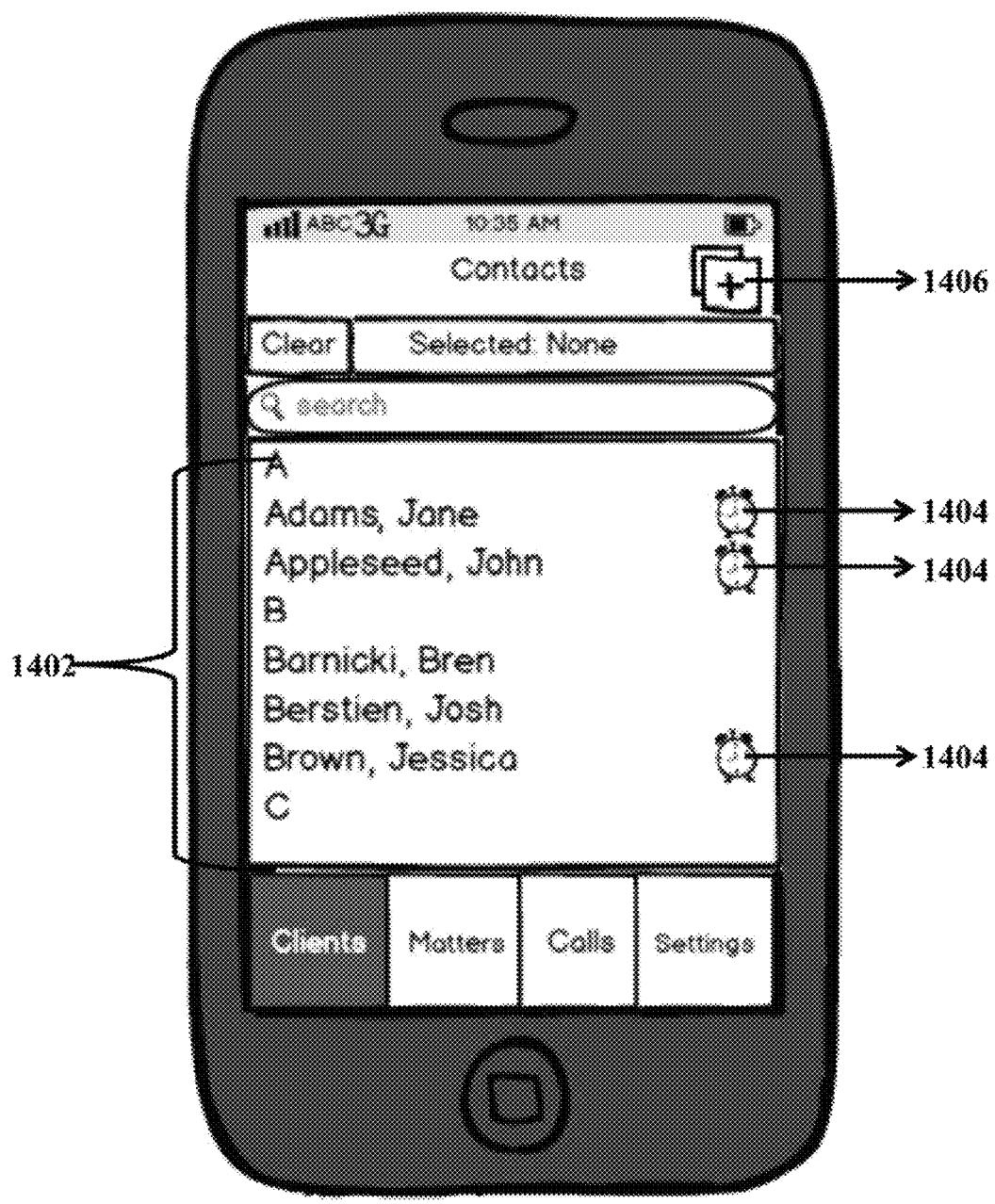
FIG. 14 shows an example of a user interface that can be presented to a user to allow the user to view and/or edit a directory of the user's clients and/or contacts in accordance with some embodiments of the disclosed subject matter.
Figure 15:
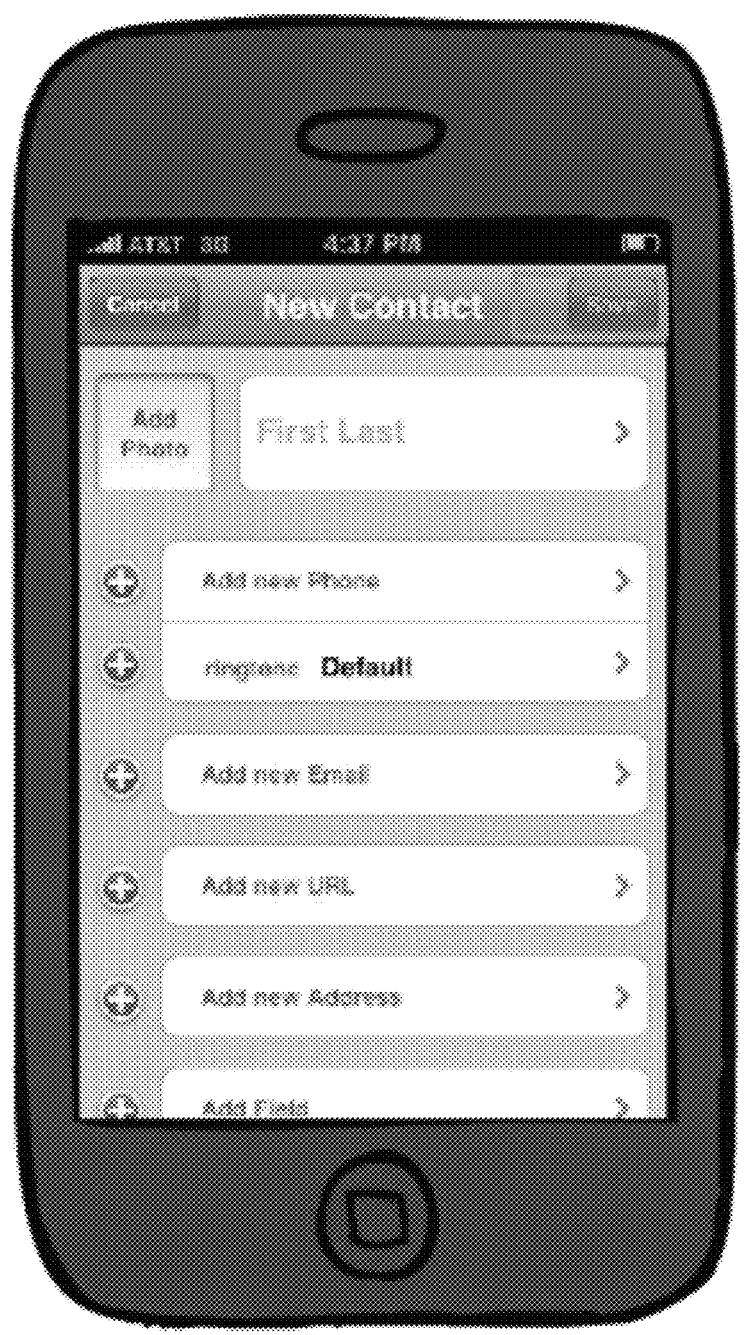
FIG. 15 shows an example of a user interface for adding a new contact to a contact directory in accordance with some embodiments of the disclosed subject matter.
Figure 16:
FIG. 16 shows an example of a user interface for designating a contact as a client contact and creating a profile for the client contact in accordance with some embodiments of the disclosed subject matter.
Figure 17:
FIG. 17 shows an example of a user interface that can be presented to a user in response to the user selecting a contact to be designated as a client contact in accordance with some embodiments of the disclosed subject matter.
Figure 18:
FIG. 18 shows an example of a user interface that can be presented to a user in response to the user activating a client profile for a selected contact in accordance with some embodiments of the disclosed subject matter.
Figure 19:
FIG. 19 shows an example of a user interface for viewing and/or editing a client profile in accordance with some embodiments of the disclosed subject matter.
Figure 20:
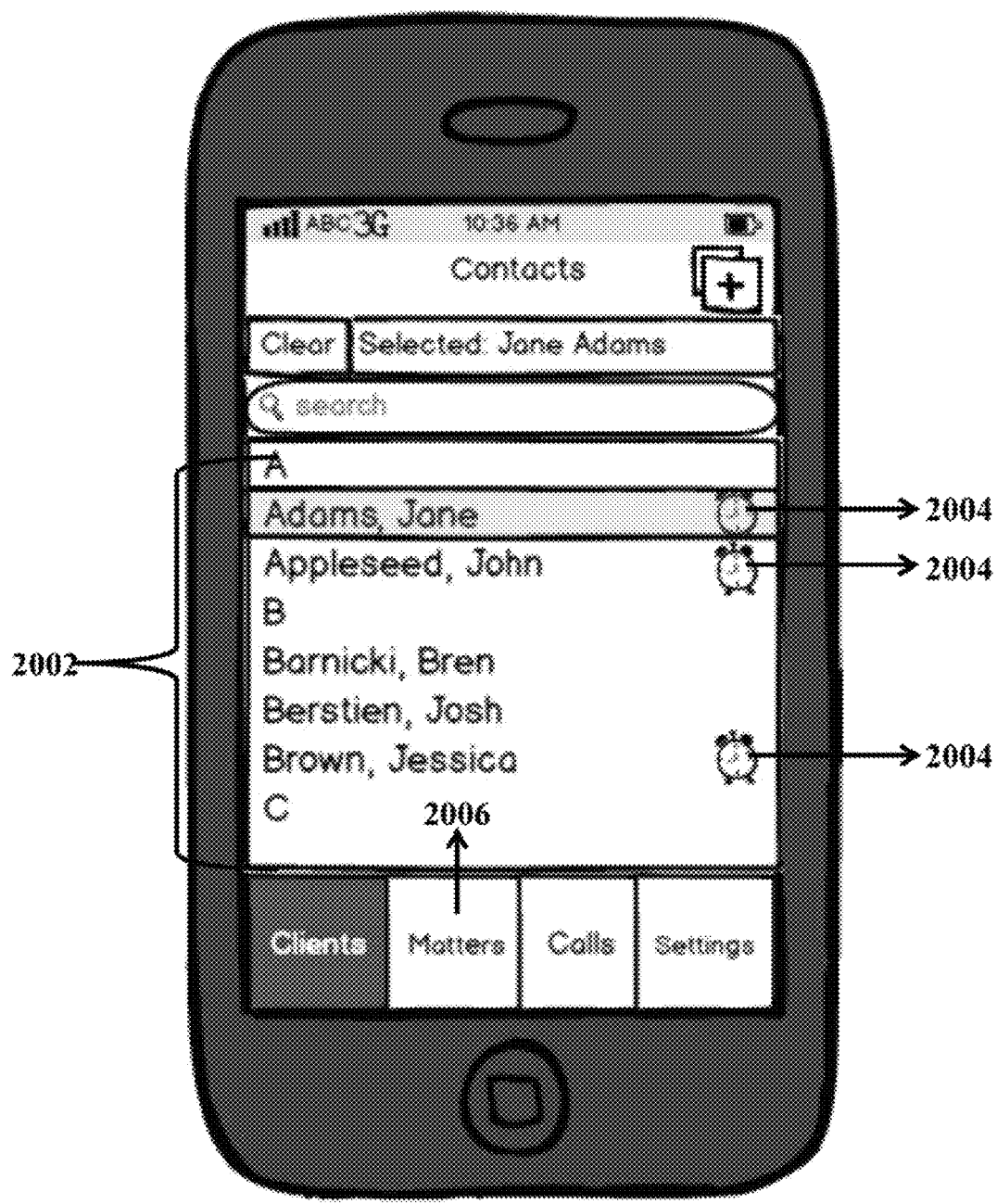
FIG. 20 shows an example of a user interface for viewing and/or editing information relating to a particular client contact in accordance with some embodiments of the disclosed subject matter.

In some embodiments, in response to the user selecting the contact to be designated as a client contact (e.g., by selecting button 1602 of interface 1600), an interface 1700 of FIG. 17 can be presented to the user. As shown, interface 1700 can include an "activate client profile" button that can allow the user to designate the selected contact as a client contact and activate a client profile for the selected contact. In some embodiments, in response to the user selecting the "activate client profile" button, an interface 1800 of FIG. 18 can be presented to the user. As shown, interface 1800 can include an "activate client profile" button that can indicate that the client profile has been activated. In some embodiments, the user can select a "back" button of interface 1800 to return to the contact directory (e.g., as shown in FIG. 14 and/or FIG. 16).

In some embodiments, the application can allow the user to view and/or edit a client profile. For example, an interface 1900 of FIG. 19 can be presented to the user in response to the user indicating a desire to view and/or edit the information relating to the client contact (e.g., by selecting a "go to contact information" button in interface 1700 of FIG. 17). Any suitable information can be entered using interface 1900. For example, as shown, interface 1900 can include one or more text fields that can allow the user to enter the name, the phone number, the home address, and other suitable information about the client contact.

In some embodiments, the application can allow the user to view and/or edit information relating to a particular client contact (e.g., such as matters relating to the client, information about calls relating to the client, the client's contact information, etc.). For example, interface 2000 of FIG. 20 can be presented to the user to allow the user to select a client contact and view information relating to the selected client contact. As shown, interface 2000 can include a directory 2002 of the user's contacts including one or more client contacts that are identified by icon(s) 2004. In some embodiments, the user can select a client contact listed in directory 2002.

Figure 21:
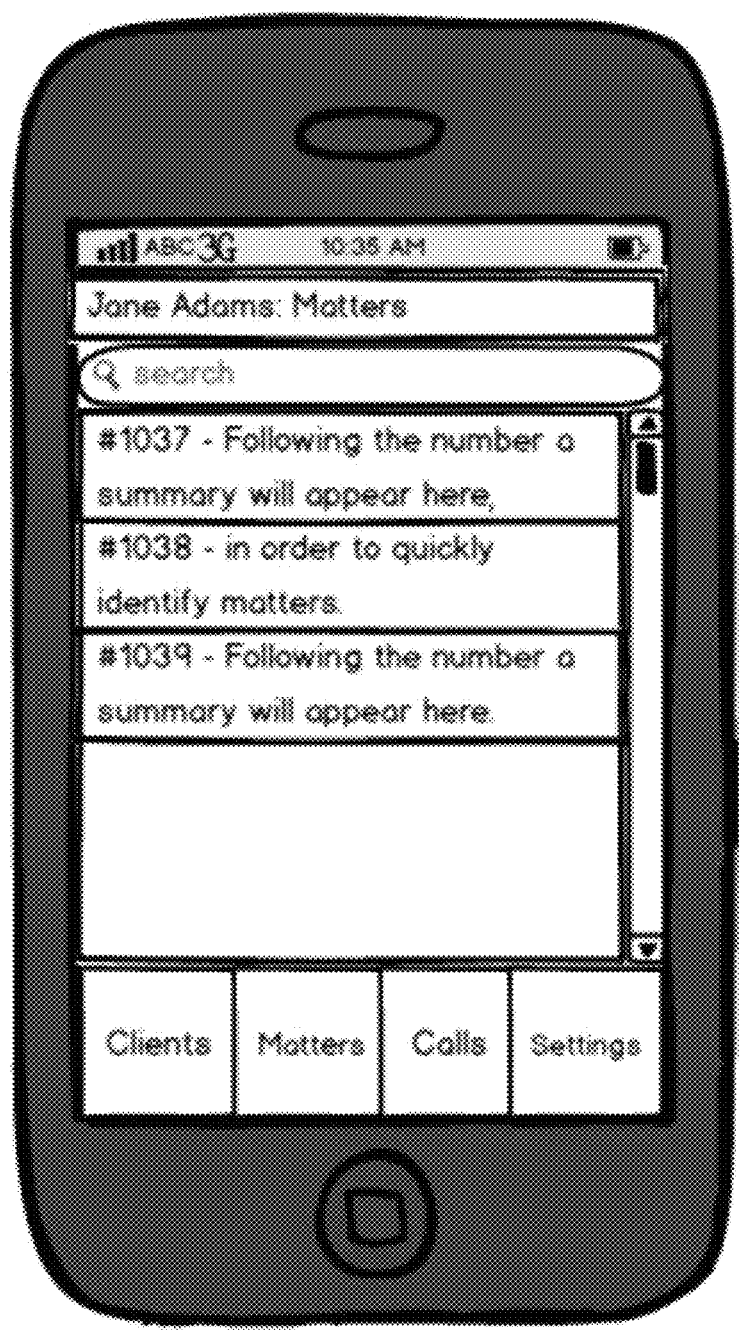
FIG. 21 shows an example of a user interface for viewing and/or editing information relating to matters/cases that are associated with a particular client contact in accordance with some embodiments of the disclosed subject matter.
Figure 22:
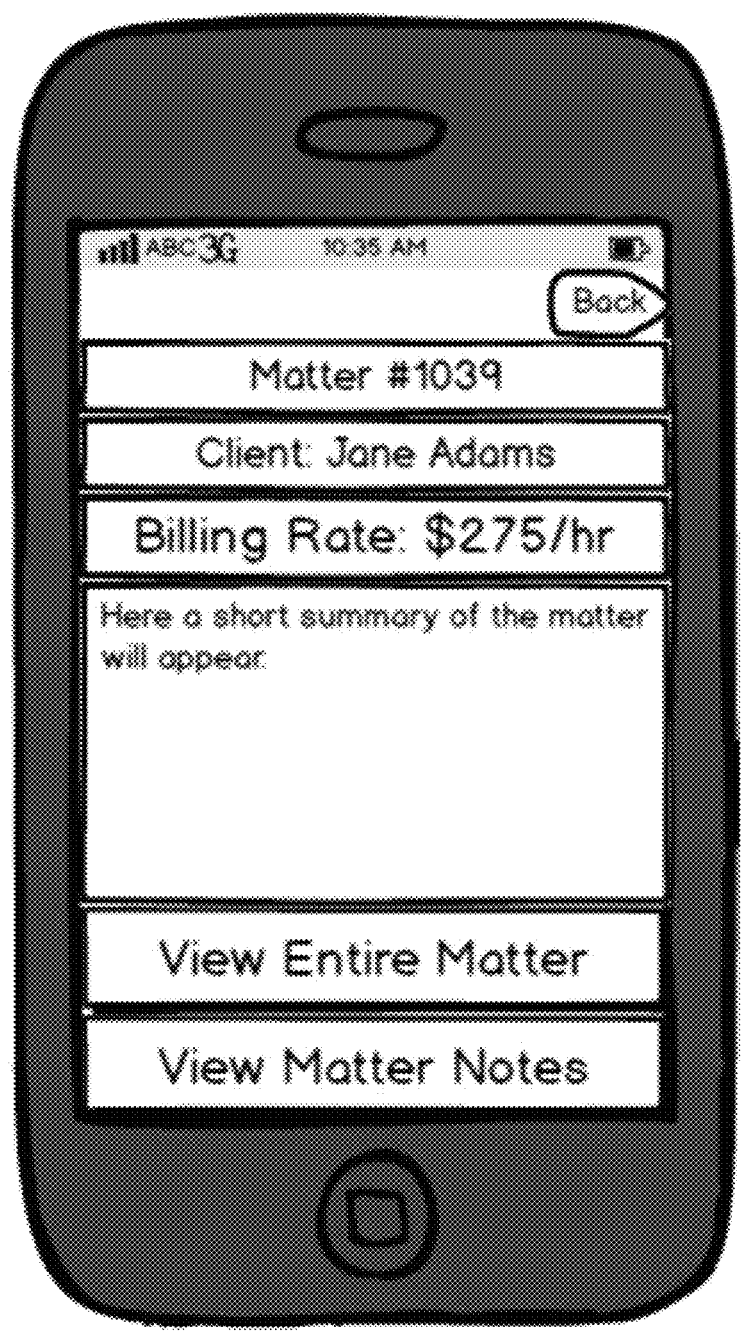
FIG. 22 shows an example of a user interface for presenting information in response to a user selecting a particular matter/case in accordance with some embodiments of the disclosed subject matter.

In some embodiments, the application can allow the user to view and/or edit information relating to matters/cases that are associated with a particular client contact. In some embodiments, as illustrated in FIG. 21, an interface 2100 can be presented to the user in response to the user indicating a desire to view and/or edit information about the matters and/or cases associated with the particular client contact (e.g., by selecting a "matters" button 2006 of FIG. 20). As shown, interface 2100 can include a list of matters/cases relating to the selected client contact. Interface 2100 can also include any suitable information relating to the matters/cases, such as an identification number corresponding to each matter/case, a summary of each matter/case, etc.

In some embodiments, the application can allow the user to view information about a particular matter/case relating to a client using one or more suitable interfaces. For example, the user can select a matter/case in interface 2100 to view information relating to the selected matter/case. In some embodiments, the application can present an interface 2200 of FIG. 22 to the user in response to the user selecting the particular matter/case. Any suitable information can be presented in interface 2200. For example, interface 2200 can include an identification number associated with the selected matter/case, the name of the client contact with which the matter/case is associated, the billing rate that should be applied to the matter/case, a summary of the matter/case, etc.

Figure 23:
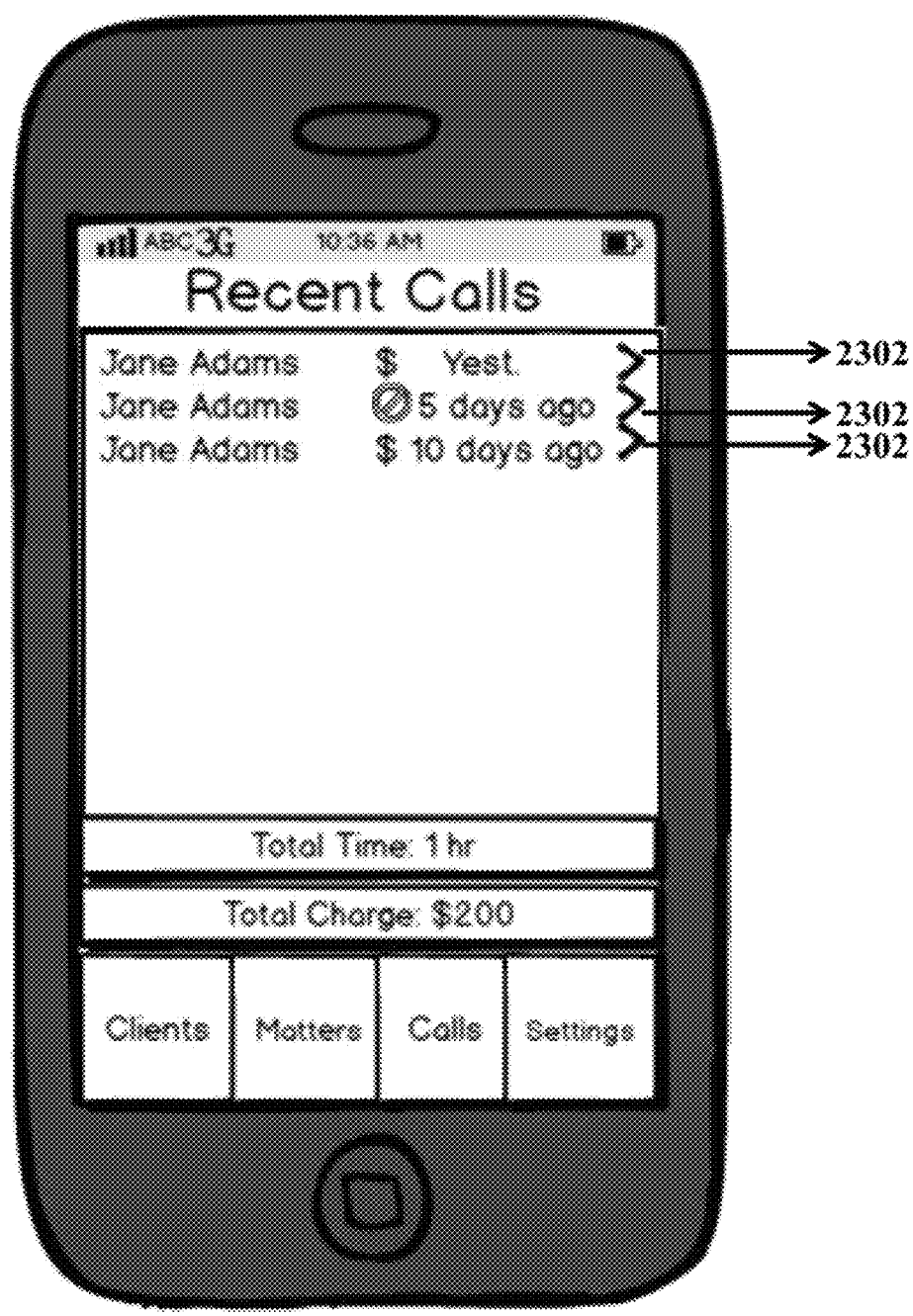
FIG. 23 shows an example of a user interface that can be presented to a user to allow the user to view information about calls relating to a particular client contact in accordance with some embodiments of the disclosed subject matter.
Figure 24:
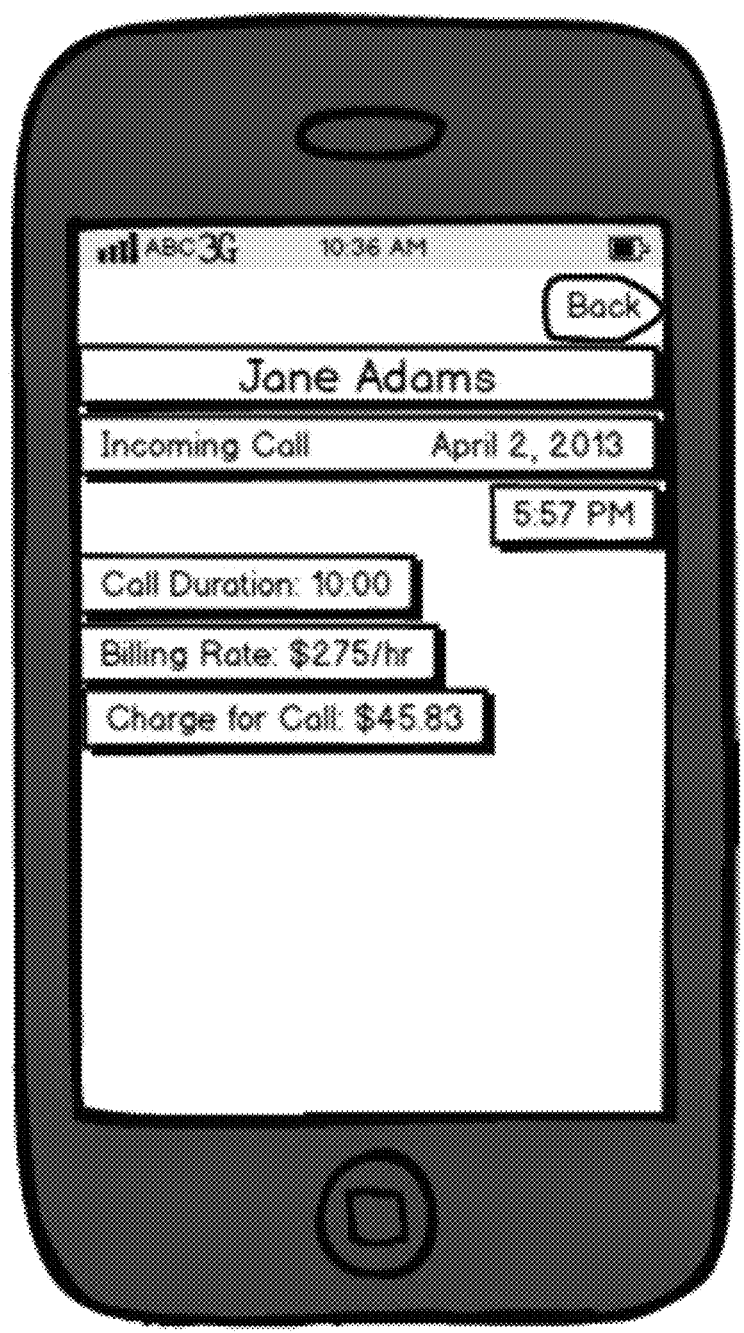
FIG. 24 shows an example of a user interface that can be presented to a user to allow the user to view and/or edit information about a selected call in accordance with some embodiments of the disclosed subject matter.

In some embodiments, the application can allow the user to view and/or edit information about calls relating to a particular client contact. For example, as illustrated in FIG. 23, an interface 2300 can be presented to the user to allow the user to view information about calls relating to a particular client contact (e.g., the client contact selected by the user using interface 2000 of FIG. 20). Any suitable information can be included in interface 2300. For example, interface 2300 can include a call log including information about one or more calls relating to the selected client contact. In some embodiments, the application can obtain such from the user device (e.g., by importing a call history stored in the user device). The interface 2300 can also include the name of the client, the time of the call, the action taken by the user with respect to each call (e.g., charging the client contact for the call at a full billing rate, charging the client contact for the conversation at a discount billing rate, ignoring the call for billing purposes, etc.), the duration of each call, the amount that has been charged for one or more of the calls, etc.

In some embodiments, the application can also allow the user to view and/or edit information relating to a particular call with a particular client contact. For example, the user can select a particular call in interface 2300 by selecting a button 2302 corresponding to the particular call. In some embodiments, an interface 2400 of FIG. 24 can be presented to the user to allow the user to view and/or edit information about the selected call. Any suitable information relating to the selected call can be presented in interface 2400. For example, interface 2400 can include information about the name of the client, a description of the call (e.g., an incoming call, an outgoing call, etc.), the date and/or time of the call, the duration of the call, the billing rate applied to the client and/or the call, the charge for the call, etc.

Figure 25:
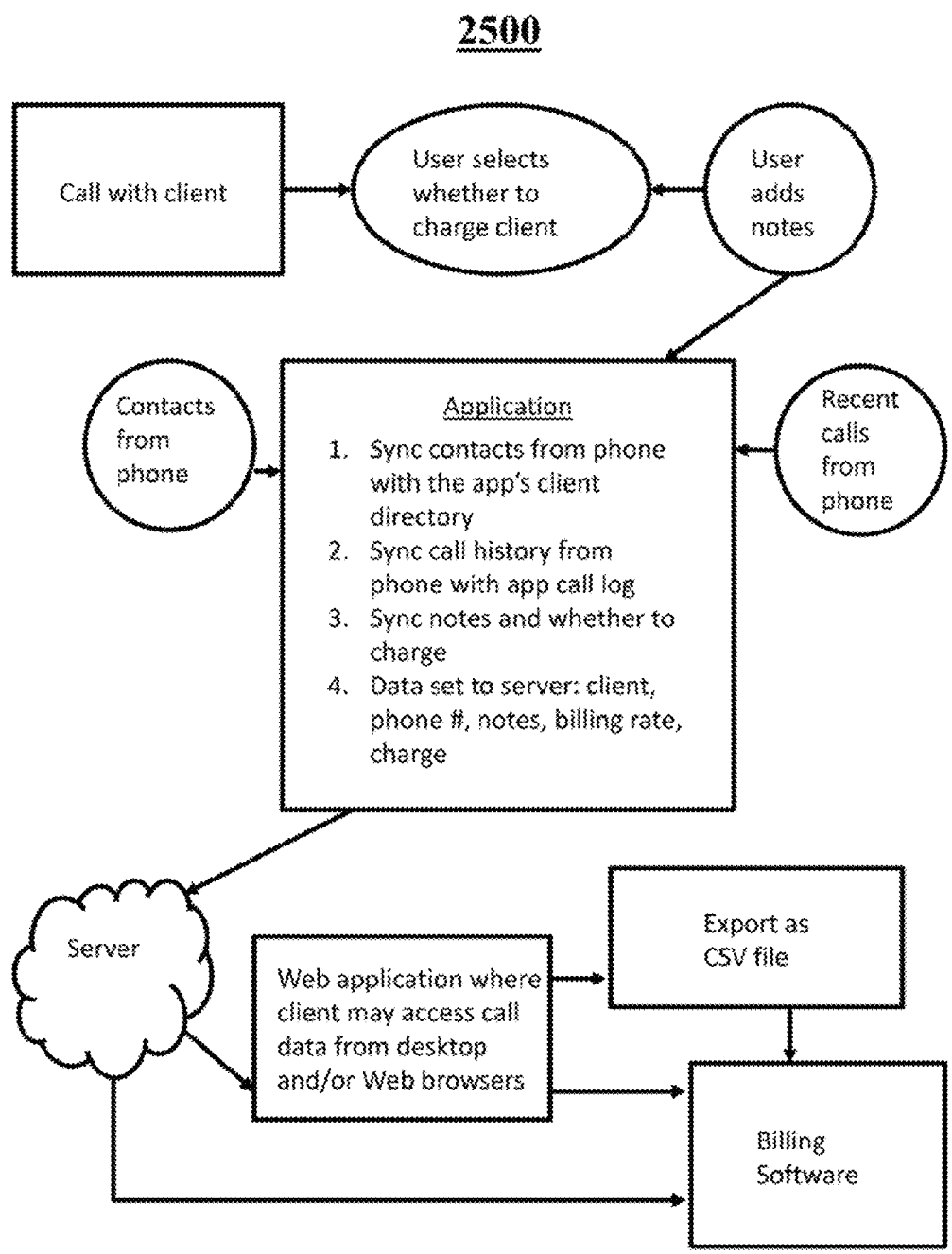
FIG. 25 shows an example of a system for implementing an application for tracking phone calls with clients in accordance with some embodiments of the disclosed subject matter.

In some embodiments, the application can be implemented as illustrated in FIG. 25. As shown, the application can allow the user to track time spent on a call with a client, make notes about the call, charge the client for the call at a suitable billing rate (e.g., a full billing rate, a discount billing rate, etc.), generate one or more invoices including information about one or more calls, etc. In some embodiments, the application can access suitable call data stored in a server (e.g., such as a cloud suite, etc.). For example, the application can allow the user to access such call data using a suitable user device, such as a desktop computer, a laptop computer, a tablet computer, a mobile phone, etc. In a more particular example, such call data can be accessed via a suitable browser (e.g., such as INTERNET EXPLORER, FIREFOX, CHROME, etc.).

Turning to FIGS. 26-30, an embodiment for allowing a user (e.g., a teacher, a school principal, an administrator of a school, an administrator of a school system, and/or any other suitable user) to track phone calls with parents of students and/or to create notes relating to the phone calls is described.

In accordance with some embodiments, mechanisms for tracking phone calls are provided. Generally speaking, these mechanisms can include a phone call tracking application that can allow users of the application to make a phone call to a contact (e.g., a parent of a student) in a directory, track time spent on a phone call with the contact, make notes about the phone call, and/or access information about phone calls from any suitable user device.

In some embodiments, the application can allow a user to make a phone call (e.g., voice communications, video communications, and/or multimedia communications using telephone services, voice over IP (VOIP) services, and/or any other suitable technology) with a contact (e.g., a parent of a student) using a suitable user device (e.g., a mobile phone, a tablet computer, a laptop computer, a desktop computer, and/or any other suitable user device). Upon completion of the phone call, the application can collect suitable information about the phone call. For example, the application can obtain information about the start time and/or end time of the phone call, the duration of the phone call, information about the contact, and/or any other suitable information.

In some embodiments, the application can prompt the user to provide suitable information about the phone call. In a more particular example, the application can allow the user to create one or more notes relating to the phone call.

In some embodiments, the application can obtain information about the contact and manage a profile for the contact. For example, the application can import a contact directory from any suitable source (e.g., contacts from a user device, a directory of contacts on a server of a school, and/or any other suitable source). The application can then create and/or edit a profile for the contact based on the information included in the contact directory and/or additional information relating to the contact provided by the user. In another more particular example, the application can obtain a phone call history including information about one or more phone calls from the user device. The application can then create and/or edit a call log including information about the phone calls relating to the contact (e.g., such as the duration of each phone call, the topic of each phone call, and/or any other suitable information).

In some embodiments, upon gathering the information relating to the phone call and/or to the contact, the application can save the information in a suitable storage device (e.g., a storage device in the user device, a server, and/or any other suitable storage device) and/or upload a part or all of the information to a server (e.g., such as a cloud suite). For example, the application can upload information relating to the contact, the phone number, the date and/or time of the phone call, the duration of the phone call, the notes relating to the phone call, and/or any other suitable information to the server.

In some embodiments, the application can access suitable data relating to one or more phone calls stored in the server. In some embodiments, the application can extract the data from the server in a suitable manner. For example, in some embodiments, the data can be analyzed before extraction to indicate any suitable metric relating to phone calls, such as a total number of phone calls made and/or received by a user, an average duration of phone calls made and/or received by a user over a particular time period, an average number of phone calls made and/or received by all of the teachers at a particular school over a particular time period, and/or any other suitable metrics.

These and other features for tracking phone calls with parents are described herein by way of the examples shown in FIGS. 26-30.

Figure 26:
FIG. 26 shows an example of a user interface for prompting a user to log into the user's account in accordance with some embodiments of the disclosed subject matter.

In some embodiments, the application can prompt a user to log into the user's account to make phone calls, view and/or edit a directory of contacts, view a phone call log, and/or view and/or edit notes relating to phone calls. For example, as illustrated in FIG. 26, an interface 2600 can be presented to the user to allow the user to log into the user's account by entering suitable credentials (e.g., a username, a password, and/or any other suitable credentials).

In some embodiments, an account can be associated with any suitable entity. For example, in some embodiments, an account can be associated with a teacher, and the directory of contacts can correspond to students of the teacher. As another example, in some embodiments, an account can be associated with a principal of a school. As a more particular example, the directory of contacts can correspond to teachers at the school as well as students at the school, and the phone call log can correspond to phone calls made and/or received by any teacher at the school. As yet another example, in some embodiments, an account can be associated with an administrator of a school system. As a more particular example, the directory of contacts can correspond to principals, teachers, and/or students within the school system, and the phone call log can correspond to phone calls made and/or received by teachers at a particular school.

In some embodiments, the application can allow the user to view and/or edit a directory of contacts. In some embodiments, an interface 2700 of FIG. 27 can be presented in response to the user indicating that the user wants to view and/or edit a directory of contacts. In some embodiments, the directory of contacts can be imported from the user's contact directory stored in a user device. Additionally or alternatively, in some embodiments, the directory of contacts can be imported from a contact directory stored in an external device (e.g., a school's server, a cloud suite, and/or any other suitable device).

Figure 27:
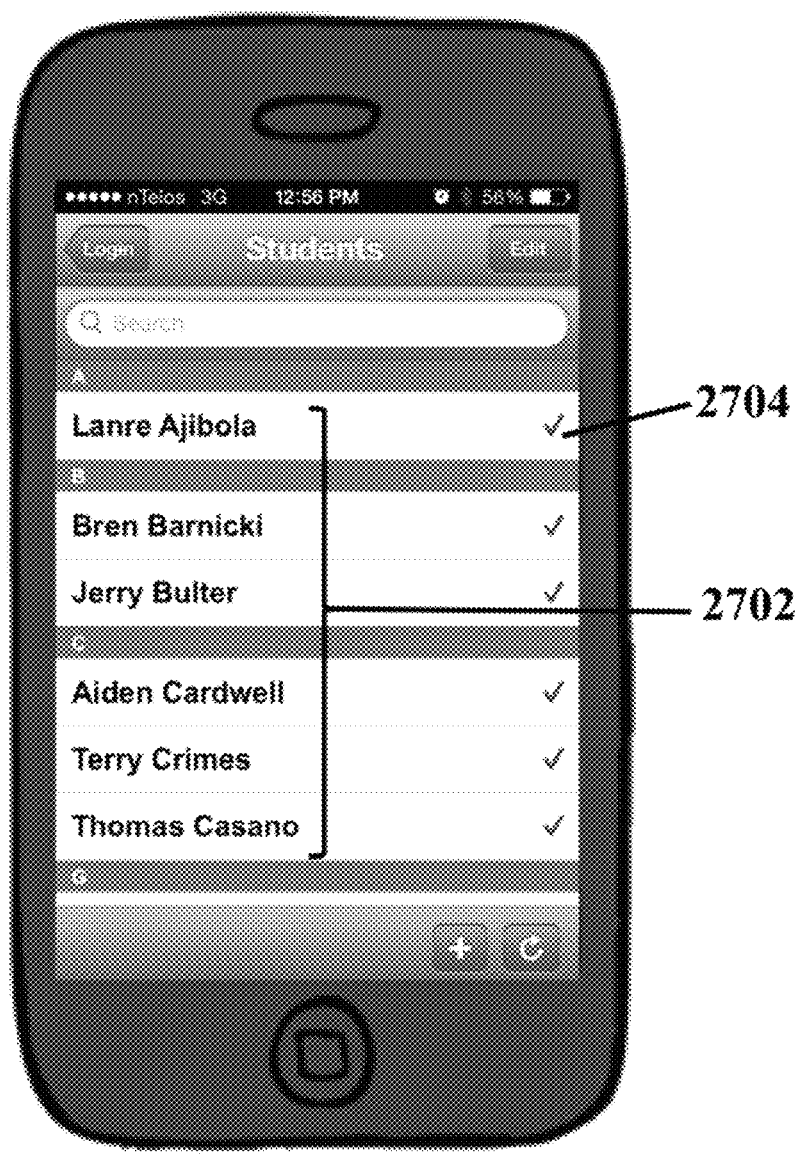
FIG. 27 shows an example of a user interface that can be presented to a user to allow the user to view and/or edit a directory of contacts in accordance with some embodiments of the disclosed subject matter.

In some embodiments, each of the contacts in the directory can correspond to a student (e.g., a student in the user's class). In some embodiments, interface 2700 can include a list of students 2702 and a selection mechanism 2704. List of students 2702 can include any suitable information and can be presented in any suitable manner. For example, list of students 2702 can include a full name (e.g., first name, middle name, and/or last name) of a student. As another example, in some embodiments, list of students 2702 can be presented alphabetically, as shown in FIG. 27. Selection mechanism 2704 can allow a user to select a particular contact (e.g., a particular student) from the directory, for example, to make a phone call to the contact, to view and/or edit notes relating to phone calls with the contact, and/or for any other suitable purpose. In some embodiments, selection mechanism 2704 can include a selectable icon (e.g., a check mark, an arrow, a circle, and/or any other suitable icon), as shown in FIG. 27. In some embodiments, selection mechanism 2704 can include any suitable text, images, icons, and/or any other suitable content. In some embodiments, a name of a contact can be selectable; in some embodiments, selection mechanism 2704 can be omitted.

Figure 28:
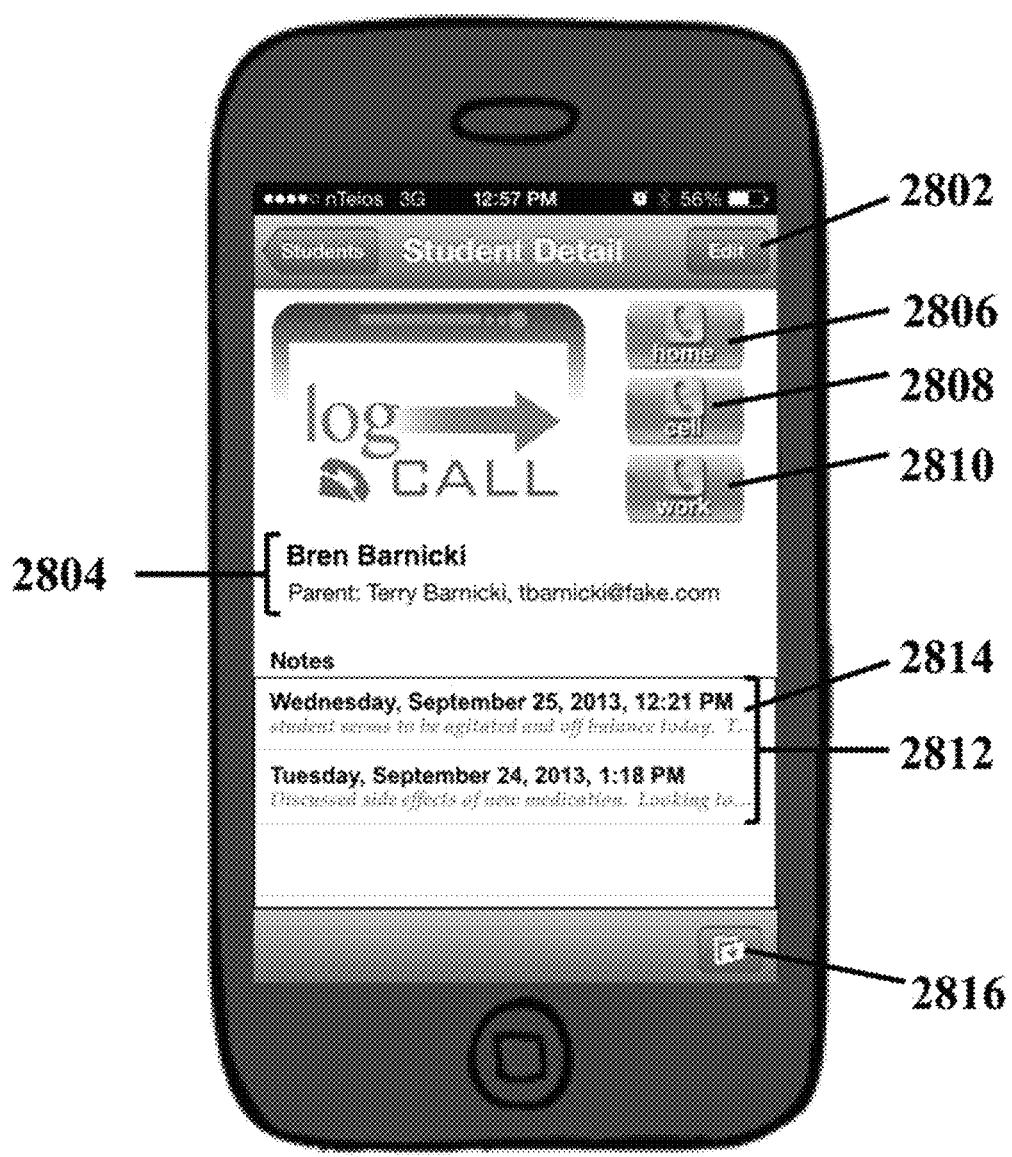
FIG. 28 shows an example of a user interface that can be presented to a user to allow the user to view and/or edit information associated with a particular contact in accordance with some embodiments of the disclosed subject matter.

In some embodiments, the application can allow the user to view and/or edit information associated with a particular contact (e.g., a particular student). In some embodiments, as illustrated in FIG. 28, an interface 2800 can be presented to the user in response to the user indicating that the user wants to view and/or edit information associated with a particular contact. For example, in some embodiments, interface 2800 can be presented in response to determining that a selection mechanism (e.g., selection mechanism 2704 as shown in and described in connection with FIG. 27) associated with a particular contact has been selected. As shown, interface 2800 can include an edit button 2802, contact information 2804, make phone call buttons 2806, 2808, and 2810, set of notes 2812, and add note button 2816.

Edit button 2802 can allow a user to indicate that the user wants to edit information associated with the particular contact. The information can include any suitable information, such as one or more names of parents and/or guardians associated with a student, one or more email addresses associated with a parent and/or a student, one or more phone numbers associated with a parent and/or a student, one or more reminders (e.g., a reminder to talk to a student, a reminder to call a parent, and/or any other type of reminder) associated with the particular contact, and/or any other suitable information. In some embodiments, edit button 2802 can be a selectable user interface component, as shown in FIG. 28. In some embodiments, edit button 2802 can include any suitable text, images, icons, graphics, and/or any other suitable content.

Contact information 2804 can indicate any suitable information associated with the particular contact. For example, as shown in FIG. 28, contact information 2804 can indicate a name of a student, a name of a parent, and/or an email address associated with the particular contact. As another example, in some embodiments, contact information 2804 can indicate one or more ideal times to call the particular contact, a name of a school associated with the particular contact, and/or any other suitable information. In some embodiments, one or more items of contact information 2804 can be selectable. For example, in some embodiments, selection of an email address can cause an email client to open. As a more particular example, in some embodiments, selection of an email address can cause an email client associated with a particular email address of the user (e.g., a professional email address) to open.

Make phone call buttons 2806, 2808, and 2810 can allow a user to make a phone call to the particular contact. In some embodiments, each of make phone call buttons 2806, 2808, and/or 2810 can be associated with a different phone number for the particular contact, for example, a home phone number, a mobile phone number, and/or a work phone number, as shown in FIG. 28. In some embodiments, make phone call buttons 2806, 2808, and/or 2810 can be selectable user interface components. In some embodiments, selection of any of make phone call buttons 2806, 2808, and/or 2810 can cause a phone call to the corresponding phone number to be made. In some embodiments, the application can allow the user to indicate whether the phone call should be made using a plan associated with a user device, using VOIP technology, and/or using any other suitable phone call technology. Make phone call buttons 2806, 2808, and/or 2810 can include any suitable text, images, icons, graphics, and/or any other suitable content. Although three make phone call buttons are shown in FIG. 28, any suitable number, including none, can be included.

Set of notes 2812 can indicate any notes associated with the particular contact. For example, set of notes 2812 can include individual notes associated with phone calls, such as individual note 2814. Any suitable number of individual notes (including none) can be presented in set of notes 2812. Individual notes can be presented within set of notes 2812 in any suitable manner. For example, as shown in FIG. 28, individual note 2814 can include a date and/or time associated with the note (e.g., a date and/or a time of a phone call). As another example, in some embodiments, individual note 2814 can include the contents of the note and/or a subset of the contents of the note. In some embodiments, individual note 2814 can be selectable. In some embodiments, selection of individual note 2814 can allow a user to view the note in full and/or edit the note.

In some embodiments, set of notes 2812 can include notes created by a user other than the user of the application. For example, in some embodiments, a note included in set of notes 2812 can be authored by another teacher, a principal of a school, a parent of a student, and/or any other suitable person. In such instances, notes created by users other than the user of the application can be automatically downloaded from a server and presented in set of notes 2812.

Add note button 2816 can be any suitable selection mechanism which can allow a user to add a note associated with the particular contact. For example, as shown in FIG. 28, add note button 2816 can be a selectable user interface component. In some embodiments, add note button 2816 can include any suitable text, images, icons, graphics, and/or any other suitable content. In some embodiments, add note button 2816 can be omitted.

In some embodiments, the application can allow the user to add a note, view an existing note, and/or edit an existing note. For example, an interface 2900 of FIG. 29 can be presented to the user in response to the user indicating that the user wants to add, view, and/or edit notes. As a more particular example, interface 2900 can be presented in response to determining that add note button 2816 shown in and described in connection with FIG. 28 was selected. As another more particular example, interface 2900 can be presented in response to determining that an individual note, for example, individual note 2814 as shown in and described in connection with FIG. 28, was selected. As shown, interface 2900 can include note text 2902 and a keypad 2904.

Figure 29:
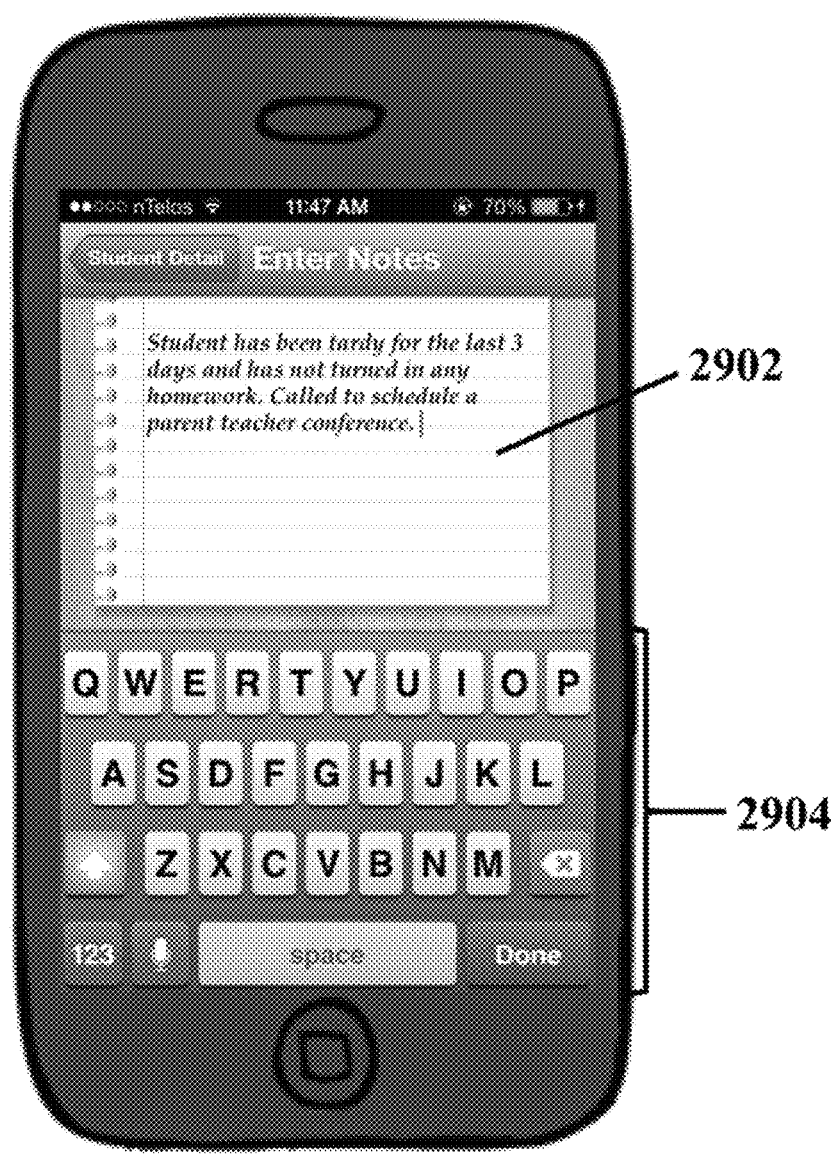
FIG. 29 shows an example of a user interface for adding, viewing, and/or editing a note in accordance with some embodiments of the disclosed subject matter.

Note text 2902 can display the contents of the note in any suitable manner. For example, as shown in FIG. 29, note text 2902 can include a block of text (e.g., text entered by the user). In some embodiments, any suitable amount of text can be included.

In some embodiments, notes can be added and/or edited in any suitable manner. For example, notes can be entered using keypad 2904. As another example, in some embodiments, a note can be recorded as a voice memo through a microphone associated with the user device. As yet another example, in some embodiments, any suitable images and/or documents can be uploaded to the note. In some embodiments, a note can be saved with any suitable technique or combination of techniques. For example, in some embodiments, a save button (not shown) can be presented in interface 2900, selection of which can cause the note to be saved (e.g., to a user device, to a server, to a cloud suite, and/or to any other suitable device). As another example, in some embodiments, a note can be saved automatically at any suitable frequency (e.g., every ten seconds, every thirty seconds, every minute, and/or any other suitable frequency).

Figure 30:
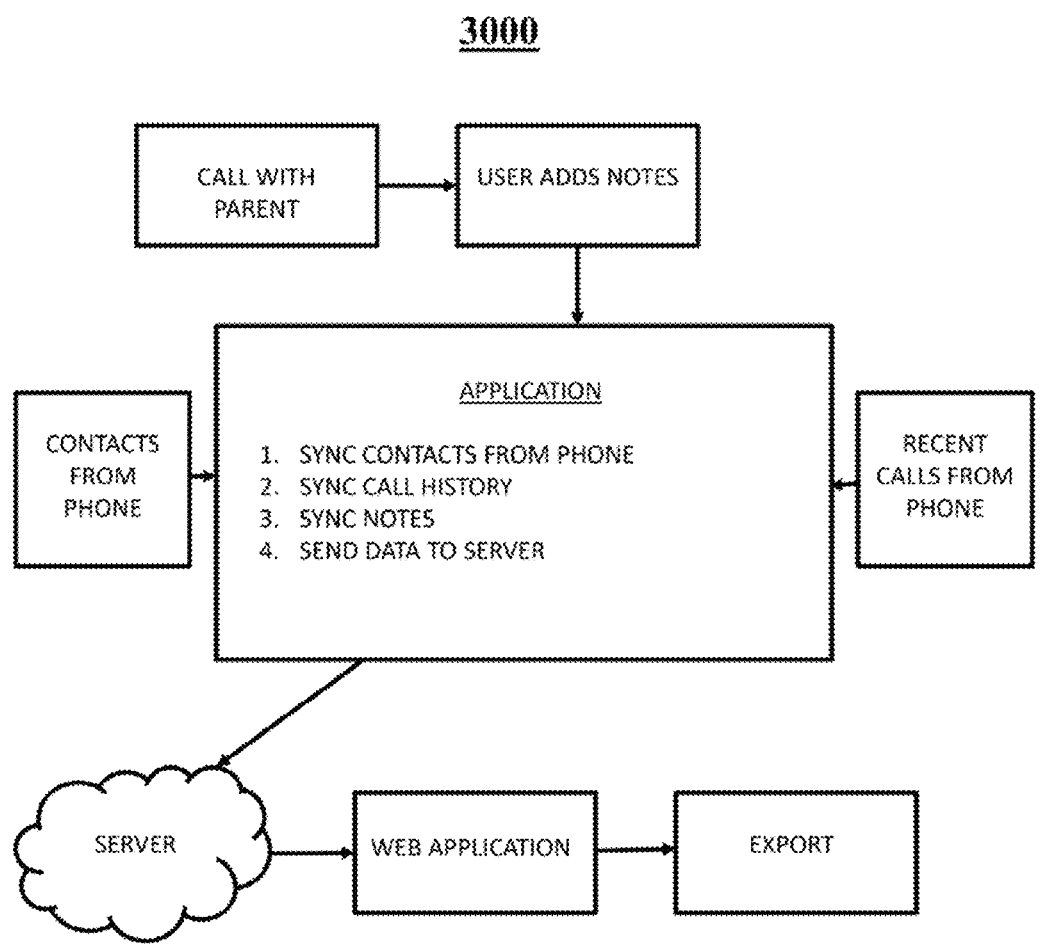
FIG. 30 shows an example of a system for implementing an application that can allow a user to synchronize contacts, information about phone calls, and/or notes in accordance with some embodiments of the disclosed subject matter.

In some embodiments, the application can be implemented as illustrated in FIG. 30. As shown, the application can allow a user to synchronize contacts, information about phone calls, and/or notes related to phone calls. In some embodiments, the application can additionally or alternatively transmit and/or store the synchronized information in a server (e.g., a cloud suite). In some embodiments, the application can allow a user to access the information (e.g., names and/or information about contacts, data about phone calls, notes associated with phone calls, and/or any other suitable information) using a suitable user device, such as a mobile phone, a tablet computer, a laptop computer, a desktop computer, and/or any other suitable user device. For example, the information can be accessed using a user device via a suitable browser (e.g., INTERNET EXPLORER, FIREFOX, CHROME, and/or any other suitable browser).

In some embodiments, a phone call made through the application can be made in a manner which appears (e.g., to a call recipient) to come from a generic number. As a particular example, in some embodiments, a phone call made by a teacher using a mobile phone can appear to come from a main phone number of the school the teacher works at.

In some embodiments, information can be exported by the application as analyzed data (e.g., analytics) related to phone calls made and/or received by one or more users. For example, in some embodiments, the application can export a total number of phone calls made and/or received over a particular time period (e.g., a week, a month, a year, a school-year, and/or any other suitable time period). As another example, in some embodiments, the application can export data associated with durations of phone calls made and/or received (e.g., an average duration over a particular time period). As another example, in some embodiments, the application can export data associated with phone calls made to a particular contact. As a more particular example, the application can export a number of phone calls made to a particular contact, a frequency of phone calls made to a particular contact, a change in the frequency of phone calls made to a particular contact, and/or any other suitable information. As yet another example, in some embodiments, the application can export data associated with notes made by a user. As a more particular example, the application can export a number of notes created in association with a particular contact, an average length of notes created in association with a particular contact, and/or any other suitable measure. Data can be exported in any suitable manner. For example, in some embodiments, data can be exported as a text file, a CSV file, and/or any other suitable file type.

In some embodiments, exported data can be collapsed and/or averaged over any suitable group. For example, in some embodiments, exported data can relate to phone calls made and/or received by a particular teacher. As a more particular example, in some embodiments, the exported data can relate to phone calls made and/or received by a particular teacher associated with any of the teacher's students. As another particular example, in some embodiments, the exported data can relate to phone calls made and/or received by a particular teacher associated with a particular class. As another example, in some embodiments, exported data can relate to phone calls made and/or received by a group of teachers (e.g., first-grade teachers, math teachers, all of the teachers, and/or any other suitable group) at a particular school.

Turning to FIGS. 32-48, mechanisms for allowing a user (e.g., a doctor, a nurse, a physician's assistant, a dentist, and/or any other suitable user) to track phone calls with patients and/or to create notes relating to the phone calls are described.

In accordance with some embodiments, mechanisms for tracking phone calls are provided. Generally speaking, these mechanisms can include a phone call tracking application that can allow users of the application to make a phone call to a contact (e.g., a patient), track time spent on a phone call with the contact, make notes about the phone call, schedule a follow-up call, and/or access information about phone calls from any suitable user device. In some embodiments, the mechanisms can allow information related to the phone call (e.g., date of the phone call, duration of the phone call, and/or any other suitable information) and/or any notes to be transmitted to a server (e.g., a cloud suite, a remote storage device, an external server, and/or any other suitable device). In some embodiments, the stored information and/or the transmission of the information to the server can be encrypted and/or password-protected.

In some embodiments, the system for tracking phone calls can be compliant with the United States Health Insurance Portability and Accountability Act (HIPAA). For example, in some embodiments, a server and/or cloud suite on which any information and/or created notes related to patients is stored can be compliant with HIPAA regulations. As another example, in some embodiments, an electronic medical record (EMR) and/or a server on which an EMR is stored can be compliant with HIPAA regulations. As yet another example, in some embodiments, transmission of information (e.g., from a user device to a server, from one server to another server, and/or any other transmission of information) can be compliant with HIPAA regulations. As still another example, in some embodiments, storage of any suitable information associated with a patient (e.g., information related to phone call with a patient, information about a patient's health history, and/or any other suitable information) can be compliant with HIPAA regulations.

In some embodiments, the application can allow a user to make a phone call (e.g., voice communications, video communications, and/or multimedia communications using telephone services, voice over IP (VOIP) services, and/or any other suitable technology) with a contact (e.g., a patient) using a suitable user device (e.g., a mobile phone, a tablet computer, a laptop computer, a desktop computer, and/or any other suitable user device). Upon completion of the phone call, the application can collect suitable information about the phone call. For example, the application can obtain information about the start time and/or end time of the phone call, the duration of the phone call, information about the contact, and/or any other suitable information.

In some embodiments, the application can prompt the user to provide suitable information about the phone call. In a more particular example, the application can allow the user to create one or more notes relating to the phone call. In some embodiments, the created notes can include any suitable text, audio, video, images, and/or any other suitable content. For example, in some embodiments, the created notes can include a dictation (e.g., an audio recording) created by the user (e.g., as recorded by a microphone associated with a user device).

In some embodiments, the application can obtain information about the contact and manage a profile for the contact. For example, the application can import information from an EMR. The application can then create and/or edit a profile for the contact based on the information included in the EMR and/or additional information relating to the contact provided by the user. In another more particular example, the application can obtain a phone call history including information about one or more phone calls from the user device. The application can then create and/or edit a call log including information about the phone calls relating to the contact (e.g., such as the duration of each phone call, the topic of each phone call, and/or any other suitable information).

In some embodiments, upon gathering information relating to the phone call and/or to the contact, the application can save the information in a suitable storage device (e.g., a storage device in the user device, a server, and/or any other suitable storage device) and/or upload a part or all of the information to a server (e.g., such as a cloud suite). For example, the application can upload information relating to the contact, the phone number, the date and/or time of the phone call, the duration of the phone call, notes relating to the phone call, and/or any other suitable information to the server.

In some embodiments, the application can access suitable data relating to one or more phone calls stored in the server. In some embodiments, the application can extract the data from the server in any suitable manner. For example, in some embodiments, the data can be analyzed before extraction to indicate any suitable metric relating to phone calls, such as a total number of phone calls made and/or received by a user, an average duration of phone calls made and/or received by a user over a particular time period, an average number of phone calls made to and/or received from a particular patient, and/or any other suitable metric.

These and other features for tracking phone calls with patients are described herein by way of the examples shown in FIGS. 32-48.

Figure 32:
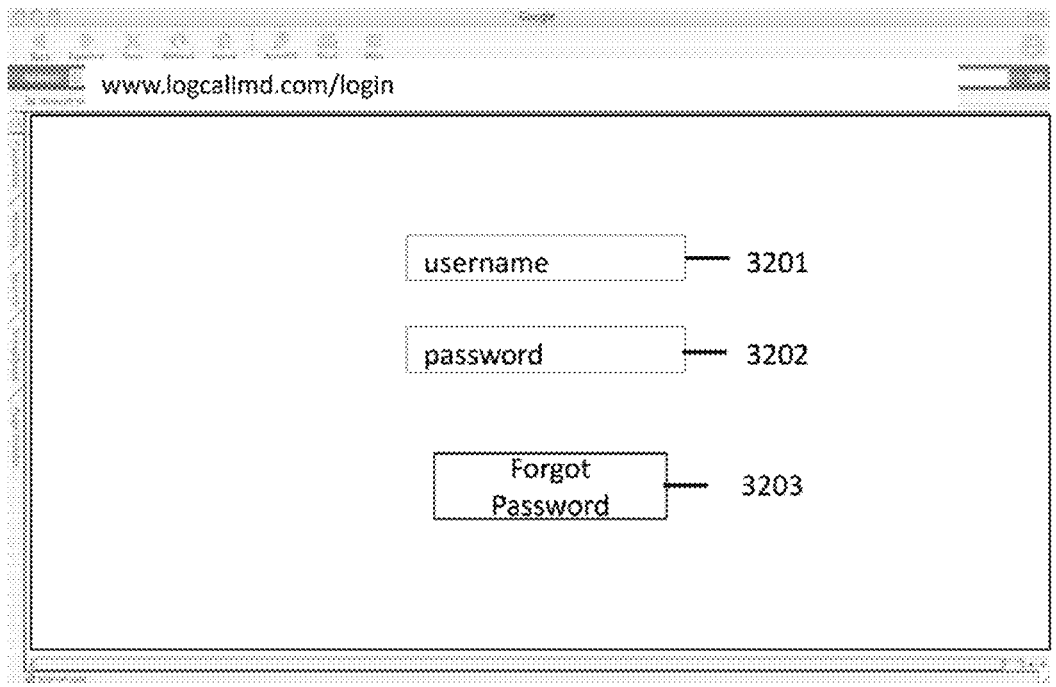
FIG. 32 shows an example of a user interface that can be presented to a user to allow the user to log into a HIPAA-compliant server in accordance with some embodiments of the disclosed subject matter.

In some embodiments, users can log into a HIPAA-compliant server (e.g., a cloud suite, a server, and/or any other suitable storage device) via any Web browser, as shown in user interface 3200 of FIG. 32. In some embodiments, an account associated with a user can be accessed when the user enters a username 3201 and/or a password 3202 in user interface 3200. In some embodiments, a forgot password input 3203 can be used to send the user (e.g., by e-mail, by text message, and/or any other suitable method) a temporary password when selected, thereby resetting the password associated with the account.

Figure 33:
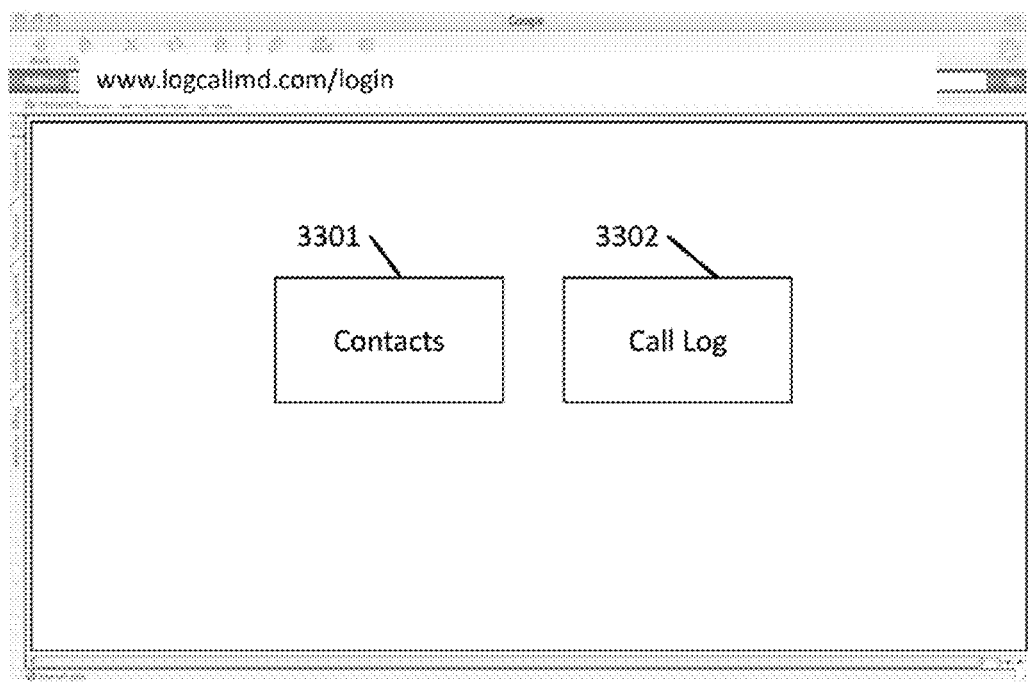
FIG. 33 shows an example of a user interface that can be presented when a user account is successfully authenticated in accordance with some embodiments of the disclosed subject matter.

Turning to FIG. 33, an example 3300 of a user interface that can be presented when a user account is successfully authenticated (e.g., using the username and/or password entered using user interface 3200) in accordance with some embodiments of the disclosed subject matter is shown. In some embodiments, user interface 3300 can include a display contacts input 3301 and a display call log input 3302. Display contacts input 3301 and display call log input 3302 can be any suitable selectable user interface controls (e.g., push buttons, selectable icons, and/or any other suitable controls). In some embodiments, selection of display contacts input 3301 can cause a listing of current contacts to be displayed. For example, in some embodiments, the listing can include all of or a subset of a doctor's patients, patients a doctor is seeing and/or has seen on a particular date and/or within a particular time period, and/or any other suitable listing of contacts. In some embodiments, selection of display call log input 3302 can cause a call history to be displayed. For example, in some embodiments, the call history can include information relating to phone calls placed within a particular time period (e.g., within the past day, within the past week, and/or any other suitable time period).

Figure 34:
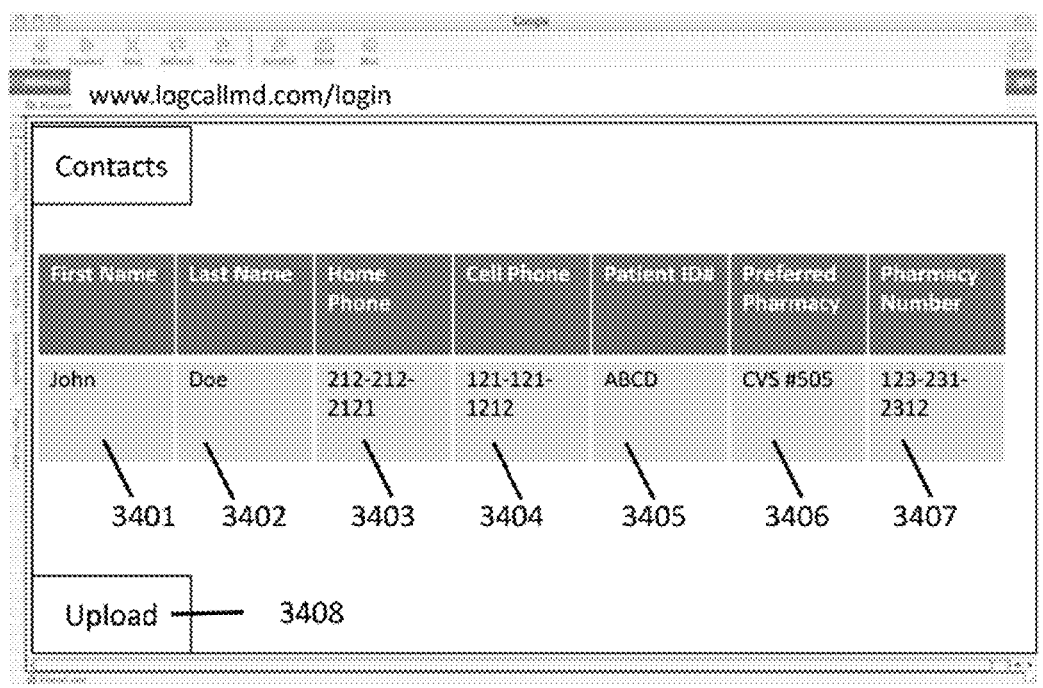
FIG. 34 shows an example of a user interface for creating a new contact and/or modifying contact information for a current contact in accordance with some embodiments of the disclosed subject matter.
Figure 35:
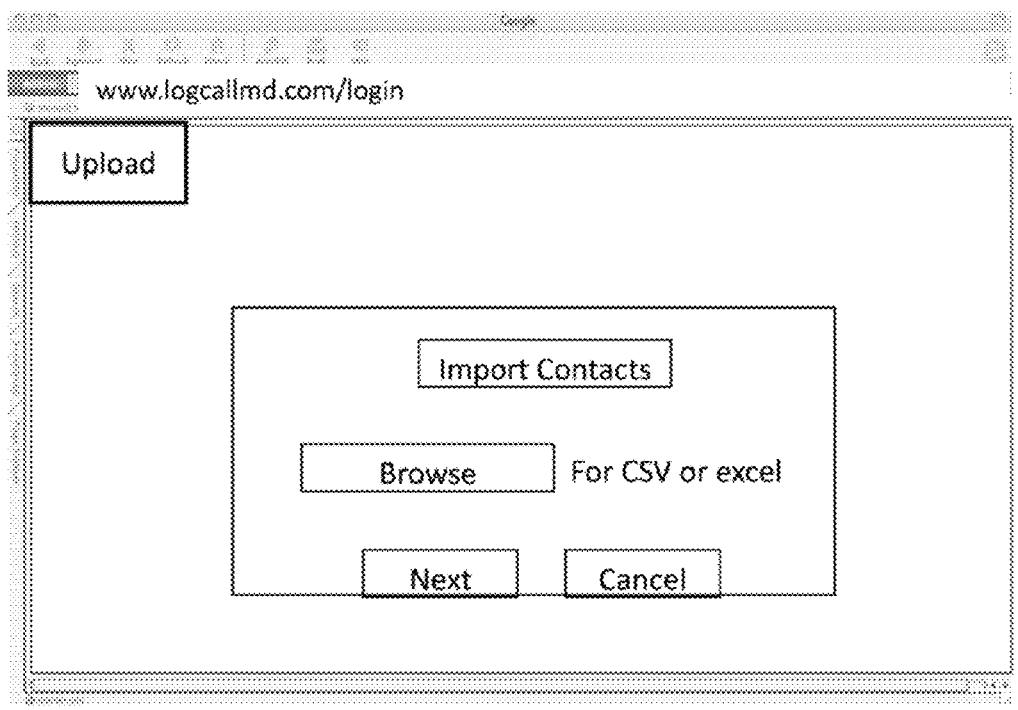
FIG. 35 shows an example of a user interface for importing contact information in accordance with some embodiments of the disclosed subject matter.

Turning to FIG. 34, an example 3400 of a user interface for creating a new contact and/or modifying contact information for a current contact in accordance with some embodiments of the disclosed subject matter is shown. In some embodiments, user interface 3400 can include fields for specifying a first name 3401, a last name 3402, a home phone number 3403, a mobile phone number 3404, a patient identification number 3405, a preferred pharmacy 3506, and/or a pharmacy phone number 3407. In some embodiments, contact information can be transmitted to a server, for example, in response to determining that upload input 3408 has been selected. In some embodiments, the transmission of the contact information can be compliant with HIPAA regulations. For example, in some embodiments, the contact information can be encrypted using any suitable encryption technology. As another example, in some embodiments, a password can be required before the information is transmitted. As yet another example, in some embodiments, a National Provider Identifier (NPI) corresponding to the user (e.g., the doctor) and/or an institution corresponding to the user (e.g., a hospital name, and/or any other suitable institution) can be required as input, and the contact information can be transmitted in association with the input NPI.

In some embodiments, contact information can be imported to any suitable device (e.g., to a mobile phone, a tablet computer, a desktop computer, and/or any other suitable device) from the server. In some embodiments, a user can select a file format associated with the imported contact information, as shown in user interface 3500 of FIG. 35. For example, in some embodiments, the contact information can be imported as a CSV file, an EXCEL file, and/or in any other suitable format.

Figure 36:
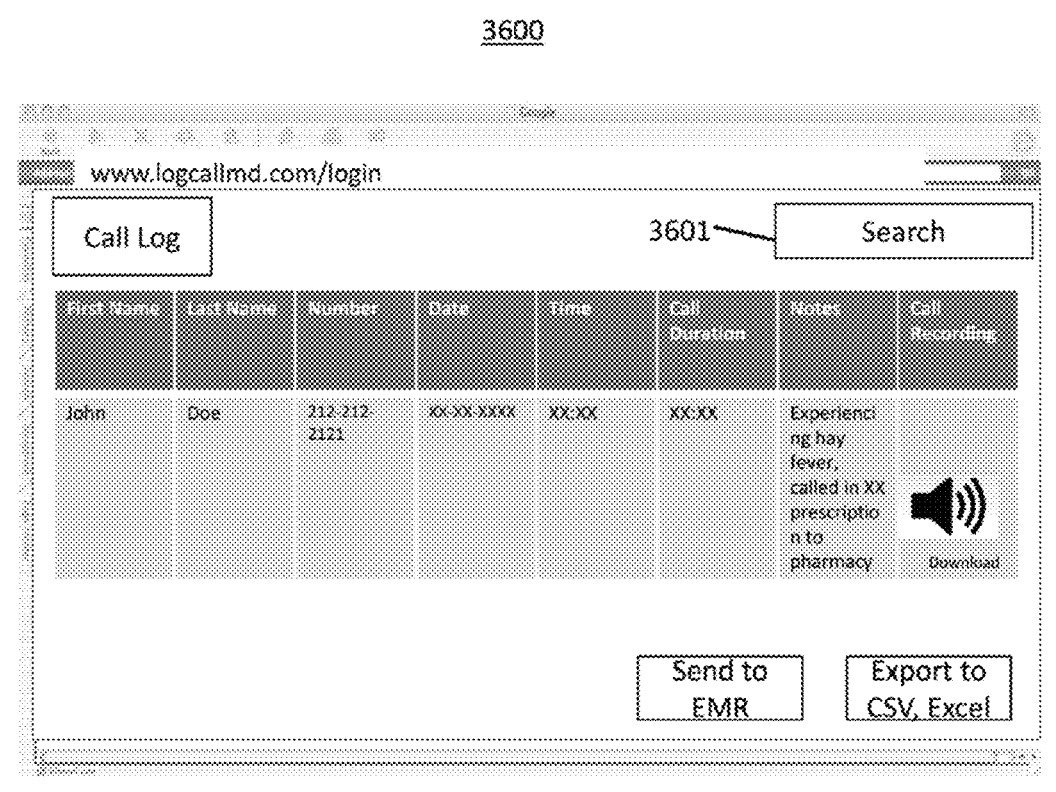

FIG. 36 shows an example 3600 of a presentation of a call log and/or call history in accordance with some embodiments. As shown in FIG. 36, in some embodiments, the call log can include a name of a patient that was called, a phone number corresponding to the patient, a date of a phone call, a time at which the phone call was placed, a duration of the phone call, any notes relating to the phone call (e.g., notes made by the user, for example, a doctor), and/or an audio recording of the phone call. In some embodiments, any one or more of the fields in the call log can be edited. For example, in some embodiments, notes relating to the call can be edited in any suitable manner (e.g., via text input, input from a microphone on a user device, input from a stylus on a touchscreen, and/or any other method). In some embodiments, the call log and any information in the call log can be exported. Additionally, in some embodiments, text within the call log can be searched, for example, using search field 3601. For example, in some embodiments, a search query (e.g., "hay fever," "John Doe," and/or any other search query) can be entered in search field 3601, and the mechanisms described herein can cause call log entries corresponding to the search query to be presented (e.g., call log entries in which a note includes the entered search query, and/or any other suitable matching entries). Note that any fields of the call log shown in FIG. 36 can be omitted in some embodiments. Additionally or alternatively, in some embodiments, any other suitable fields can be included (e.g., a field specifying a date of an upcoming appointment, a field specifying medications recently ordered, and/or any other suitable fields).

Figure 37:
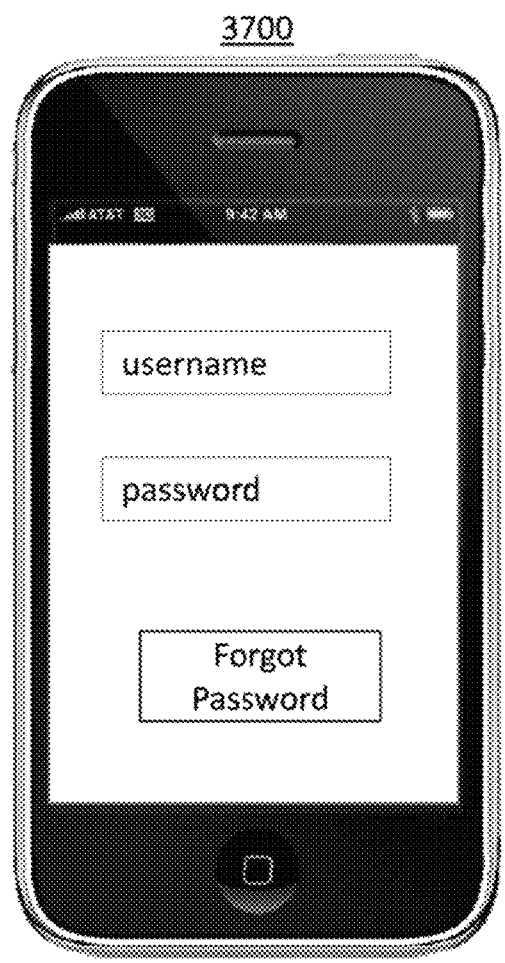
FIG. 37 shows an example of a user interface for entering a username and/or a password in accordance with some embodiments of the disclosed subject matter.
Figure 38:
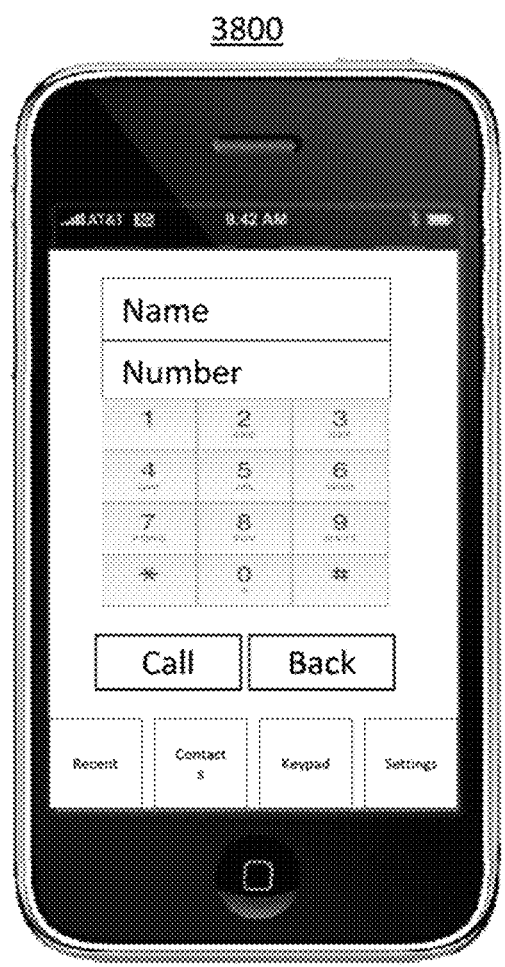
FIG. 38 shows an example of a user interface that can be presented in response to determining that a correct username and/or password have been entered in accordance with some embodiments of the disclosed subject matter.

In some embodiments, phone calls can be made through the application (e.g, a phone call to a patient, and/or to any other suitable contact). In some embodiments, entry of a correct username and/or password can be required before a phone call be made. FIG. 37 shows an example 3700 of a user interface for entering a username and/or a password in accordance with some embodiments. FIG. 38 shows an example 3800 of a user interface that can be displayed in response to determining that a correct username and/or password have been entered in user interface 3700, in accordance with some embodiments.

Figure 39:
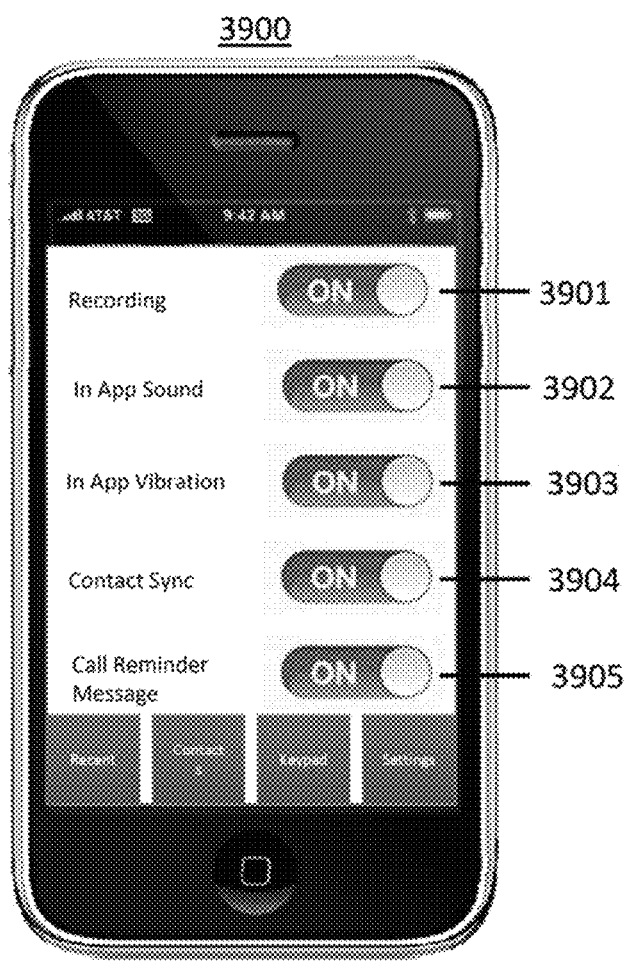
FIG. 39 shows an example of a user interface that can be displayed to receive one or more user-preferred settings in accordance with some embodiments of the disclosed subject matter.

FIG. 39 shows an example 3900 of a user interface that can be displayed to receive one or more user-preferred settings. For example, in some embodiments, user interface 3900 can include a toggle to automatically record 3901, a sound toggle 3902, a vibration toggle 3903, a contact synchronization toggle 3904, and/or a call reminder message toggle 3905. In some embodiments, selecting toggle to automatically record 3901 can cause audio from a phone call to be automatically recorded and/or stored. In some embodiments, sound toggle 3902 can cause the application to play any suitable sound and/or tone to present new messages and/or alerts. Similarly, in some embodiments, vibration toggle 3903 can cause the application to vibrate when messages and/or alerts are delivered. In some embodiments, contact synchronization toggle 3904 can cause new contacts and/or modified contact information to be automatically synchronized with a server (e.g., a cloud suite). In some embodiments, call reminder message toggle 3905 can cause an alert indicating a date and/or time for a follow-up phone call to be presented at any suitable time point prior to the scheduled time of the follow-up call (e.g., a day before, an hour before, and/or any suitable time).

In instances where audio content corresponding to a phone call is automatically recorded, the mechanisms described herein can cause the audio recording to be made and/or stored in a manner compliant with HIPAA regulations. For example, in some embodiments, the recorded audio can be automatically transmitted to a server (e.g., a cloud suite, a server that hosts an EMR associated with the corresponding patient, and/or any other suitable server). As a more particular example, in some embodiments, the recorded audio can be automatically transmitted without being stored locally on a user device from which the phone call was made. In some such embodiments, the audio content can be temporarily stored in a buffer in memory local to the user device, can be transmitted at any suitable frequency to the server, and can be deleted after transmission.

Figure 40:
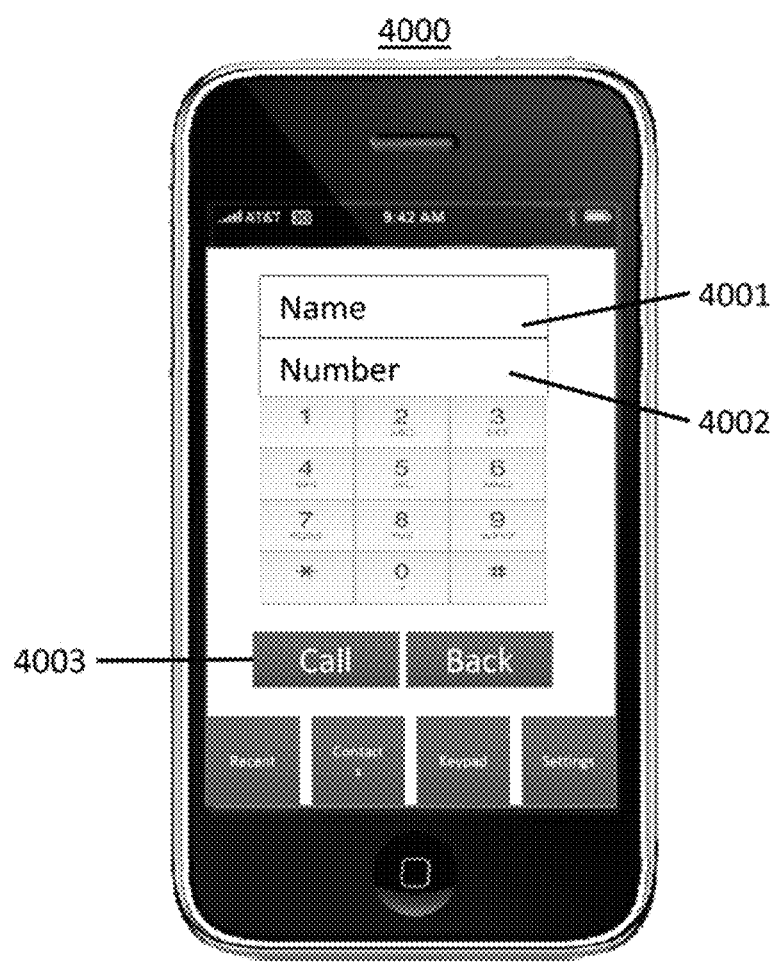
FIG. 40 shows an example of a user interface for making phone calls in accordance with some embodiments of the disclosed subject matter.

FIG. 40 shows an example 4000 of a user interface for making phone calls in accordance with some embodiments. In some embodiments, user interface 4000 can include a keypad, a name input 4001, a phone number input 4002, and a place call button 4002. In some embodiments, a phone number can be directly input, for example, through a keypad, as shown in FIG. 40. Additionally or alternatively, in some embodiments, a phone number can be copied from another source (e.g., an e-mail message, a text message, a document, and/or any other suitable source) into phone number input 4002. In some embodiments, a name of a contact can be entered into name input 4001 (e.g., directly typed, copied from another source, and/or entered in any other suitable manner), and the mechanisms described herein can cause a phone number corresponding to the entered name to be extracted from information received from a server. In some embodiments, a phone call can be initiated in response to determining that place call button 4002 has been selected (e.g., touched, clicked, and/or any other suitable selection mechanism).

Figure 41:
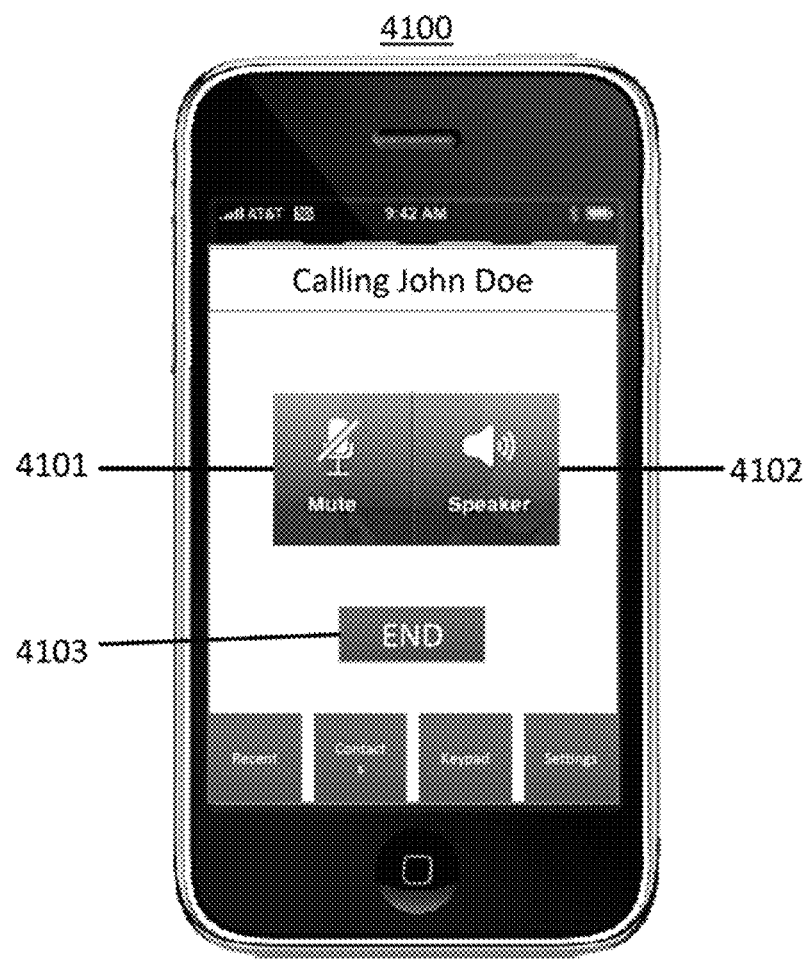
FIG. 41 shows an example of a user interface that can be presented during a phone call in accordance with some embodiments of the disclosed subject matter.

FIG. 41 shows an example 4100 of a user interface that can be presented during a phone call. In some embodiments, user interface 4100 can include one or more user interface controls that can allow a user to control audio associated with a phone call. For example, in some embodiments, a mute button 4101 can be used to turn off a microphone on the user's device. As another example, in some embodiments, speakerphone button 4102 can be used to cause audio content from the phone call to be played through external speakers of the user's device. Although not shown in FIG. 41, in some embodiments, a volume control interface can be included to allow a user to increase or decrease volume associated with the phone call. In some embodiments, an end call button 4103 can be selected to cause the phone call to end.

Figure 42:
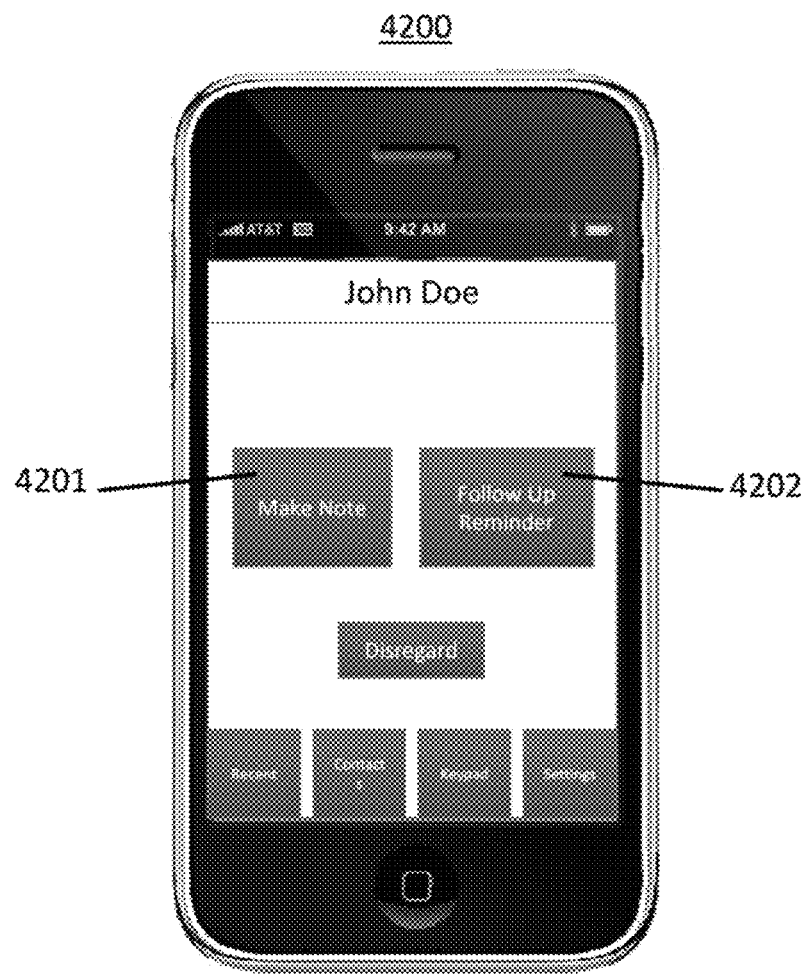
FIG. 42 shows an example of a user interface that can be presented in response to determining that a phone call has ended in accordance with some embodiments of the disclosed subject matter.

FIG. 42 shows an example 4200 of a user interface that can be presented in response to determining that a phone call has ended (e.g., upon detecting that end call button 4103 of FIG. 41 has been selected). In some embodiments, user interface 4200 can include a make note button 4201 and a make follow-up reminder button 4202. Selection of make note button 4201 can cause a user interface that allows a user to enter one or more notes to be presented, for example, as described below in connection with FIG. 43. Selection of make follow-up reminder button 4202 can cause a user interface that allows a user to enter a date at which a follow-up call is to be scheduled to be presented, for example, as described below in connection with FIG. 44.

Figure 43:
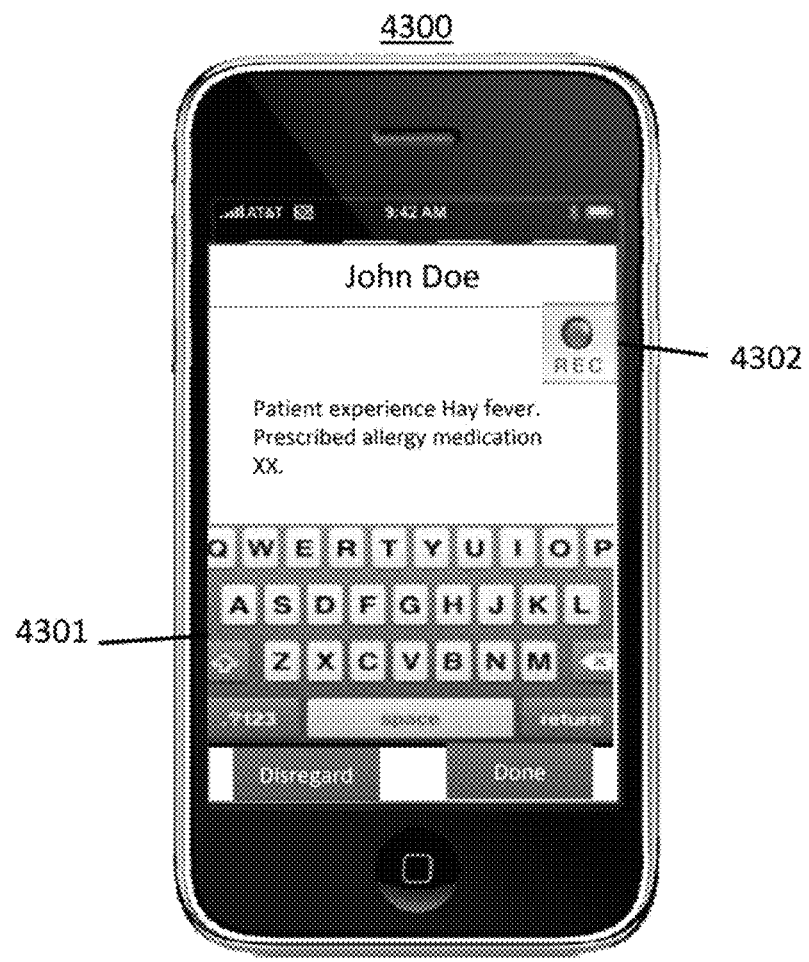
FIG. 43 shows an example of user interface for receiving user input indicating notes related to a phone call in accordance with some embodiments of the disclosed subject matter.

FIG. 43 shows an example 4300 of a user interface for receiving user input indicating notes related to a phone call. In some embodiments, user interface 4300 can be presented in response to determining that make note button 4201 has been selected. As shown, interface 4300 can include one or more entry fields in which the notes relating to the call can be displayed and/or edited. The user can add and/or edit notes relating to the call in any suitable manner. For example, the user can enter the notes as texts using a keypad (e.g., such as a keypad 4301). As another example, the user can record a voice memo and/or a dictation by selecting and holding a recording button 4302. In some embodiments, any other suitable content can be included, such as documents, images, audio recordings, videos, links to content, and/or any other suitable content. For example, in some embodiments, links to test results, medical images (e.g., X-Rays, and/or any other suitable images), and/or any other suitable information can be included. As shown in FIG. 43, notes can be saved upon determining that a "done" button has been selected. Alternatively, entered notes can be discarded upon determining that a "disregard" button has been selected.

Figure 44:
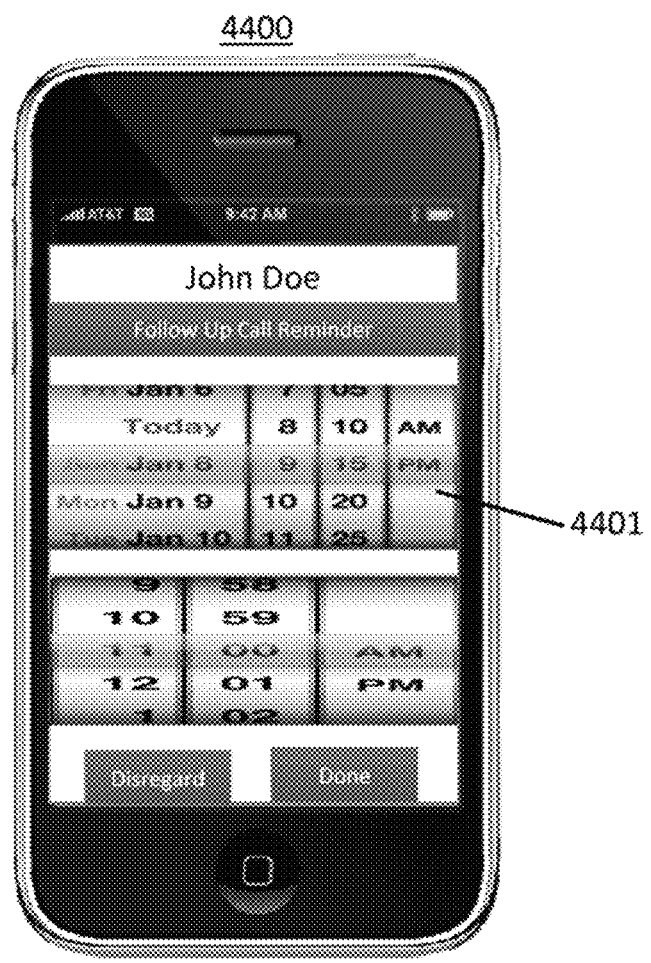
FIG. 44 shows an example of a user interface for scheduling a follow-up call with a contact in accordance with some embodiments of the disclosed subject matter.
Figure 45:
FIG. 45 shows an example of a user interface for presenting a reminder alert in accordance with some embodiments of the disclosed subject matter.

FIG. 44 shows an example 4400 of a user interface for scheduling a follow-up call with the contact. In some embodiments, user interface 4400 can include an interactive calendar 4401 that can be used to select a date and/or time for the follow-up call to be scheduled. In some embodiments, interactive calendar 4401 can include a user interface that allows a user to scroll through months, days, years, time of day, and/or any other suitable parameters. Additionally or alternatively, in some embodiments, interactive calendar 4401 can receive a date and/or time in any other suitable manner (e.g., direct entry of a date and/or time, and/or any other suitable manner). The mechanisms described herein can then cause a reminder alert to be presented at the date and time specified with interactive calendar 4401, as shown in user interface 4500 of FIG. 45.

Figure 46:
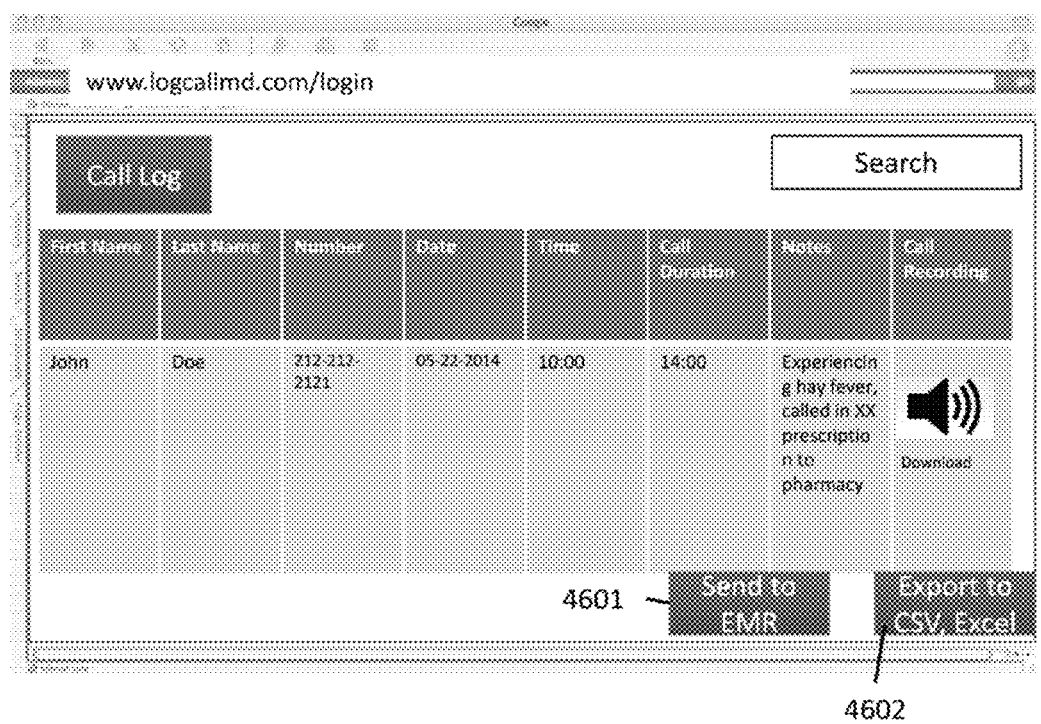
FIG. 46 shows an example of a user interface for presenting information relating to a phone call in accordance with some embodiments of the disclosed subject matter.

In some embodiments, information relating to a phone call can be transmitted to and stored on a server. In some embodiments, the information can be presented on a Web page associated with the server in response to determining that an authorized user has logged in. FIG. 46 shows an example 4600 of a user interface in which information relating to a phone call can be presented in a Web browser in accordance with some embodiments. As shown in FIG. 46, the information that is presented can include a name of a patient associated with the phone call, a phone number associated with the phone call, a date and time of the phone call, a duration of the phone call, any notes input by a user associated with the phone call, and/or an audio recording of the phone call. Additionally, in some embodiments, the server can cause the information to be collated in any suitable manner (e.g., in a CSV file, in an EXCEL file, and/or any other suitable format), and the collated information can be exported (e.g., to be saved on a user's computer), for example, in response to determining that an export button 4602 has been selected. Additionally or alternatively, in some embodiments, selection of a send to medical record button 4601 can cause the information to be transmitted to a device that stores an electronic medical record associated with the contact corresponding to the phone call.

Figure 47:
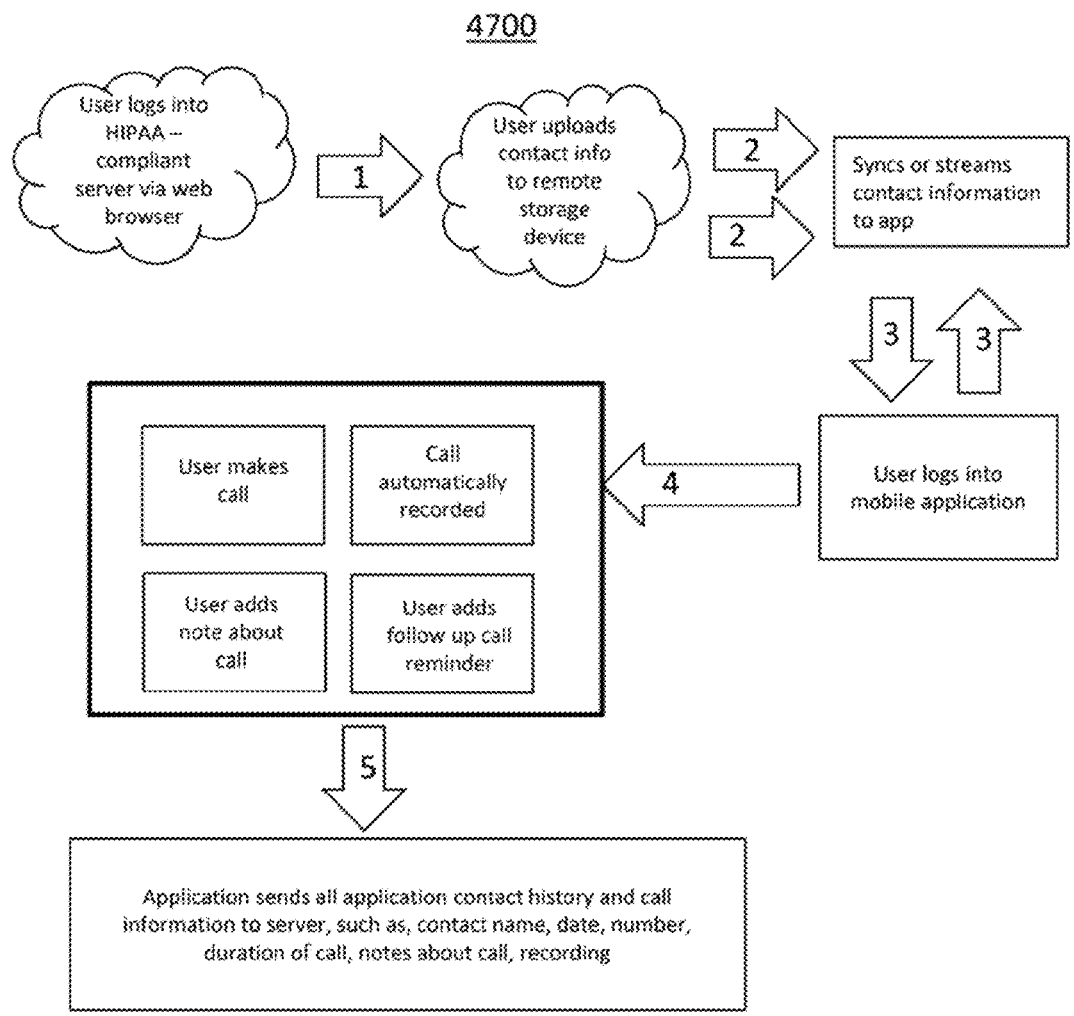
FIG. 47 shows an example of a system for making a phone call and synchronizing information related to the phone call in accordance with some embodiments of the disclosed subject matter.
Figure 48:
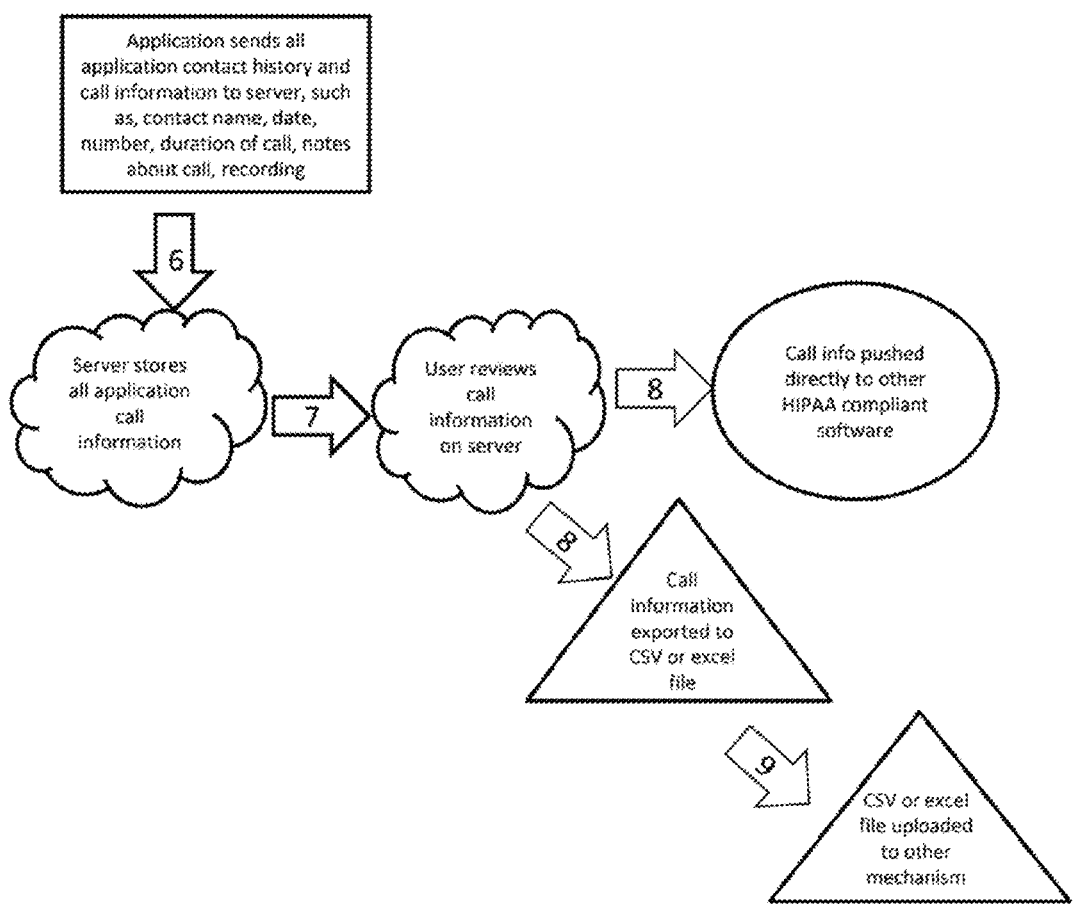
FIG. 48 shows an example of a system for exporting information related to phone calls with one or more patients from a server in accordance with some embodiments of the disclosed subject matter.

Turning to FIGS. 47 and 48, generalized block diagrams of examples 4700 and 4800 for a HIPAA compliant application and server for logging and recording phone calls, making notes about phone calls and scheduling a follow up call reminder in accordance with some embodiments of the disclosed subject matter is shown.

System 4700 shows an example of an application for allowing a user to upload and synchronize contact information, make a phone call, add notes about the phone call, add reminders for a follow-up call, and transmit the information related to the phone call (e.g., any notes, a duration of the phone call, a time and/or date of the phone call, an audio recording of the phone call, and/or any other suitable information) to a server (e.g., a cloud suite, a remote storage device, and/or any other suitable device). In some embodiments, the application can automatically transmit the information to the server. In some embodiments, any suitable subset of the information can be saved in local memory of the user device running the application.

System 4800 shows an example of a system in which information related to a phone call can be stored in memory on a server, and in which the information can be reviewed, edited, exported, and/or transmitted to a suitable electronic medical record. For example, in some embodiments, a user can log into the server using a username and/or password, and can review and/or edit information relating to one or more phone calls in a Web page provided by the server. As another example, in some embodiments, a user can cause information related to one or more phone calls to be exported in any suitable format, as described above in connection with FIG. 46. As yet another example, in some embodiments, a user can cause any suitable information to be transmitted to a second device that stores electronic medical records associated with a particular contact related to the phone call.

Note that, in some embodiments, the functions performed by the application, the server, and/or any other related device can be compliant with HIPAA regulations for storing and transmitting medical information. For example, in some embodiments, a username and/or password can be required before information related to patients, phone calls with patients, and/or any other sensitive information. As another example, in some embodiments, any collected information can be stored in an encrypted manner using any suitable encryption technology. As yet another example, in some embodiments, any transmitted information can be encrypted before transmission. As still another example, in some embodiments, any suitable handshaking protocol can be required before an application can receive and/or transmit information to a server and/or to an electronic medical record.

In some embodiments, the mechanisms described herein can cause a patient to be charged for time spent on the phone call. For example, in some embodiments, a user can specify a billing rate (e.g., in dollars per hour, and/or any other suitable billing rate), and the mechanisms described herein can calculate a total charge based on the billing rate and the duration of a phone call. In some embodiments, the mechanisms described herein can generate an invoice based on the total charge and can cause the invoice to be transmitted and/or stored on any suitable device (e.g., a server, a cloud suite, a server on which an EMR associated with the patient is stored, and/or any other suitable device). In some embodiments, a user (e.g., a doctor, an employee of a practice, and/or any other suitable user) can select a particular phone call and/or a series of phone calls related to a particular patient for which an invoice is to be generated. For example, in some embodiments, analytical information corresponding to the particular patient can be requested and presented (e.g., phone calls to the particular patient that occurred within the last week, and/or any other suitable request), and an invoice can be generated for phone calls corresponding to a selection of phone calls selected from the presented analytical information.

Figure 31:
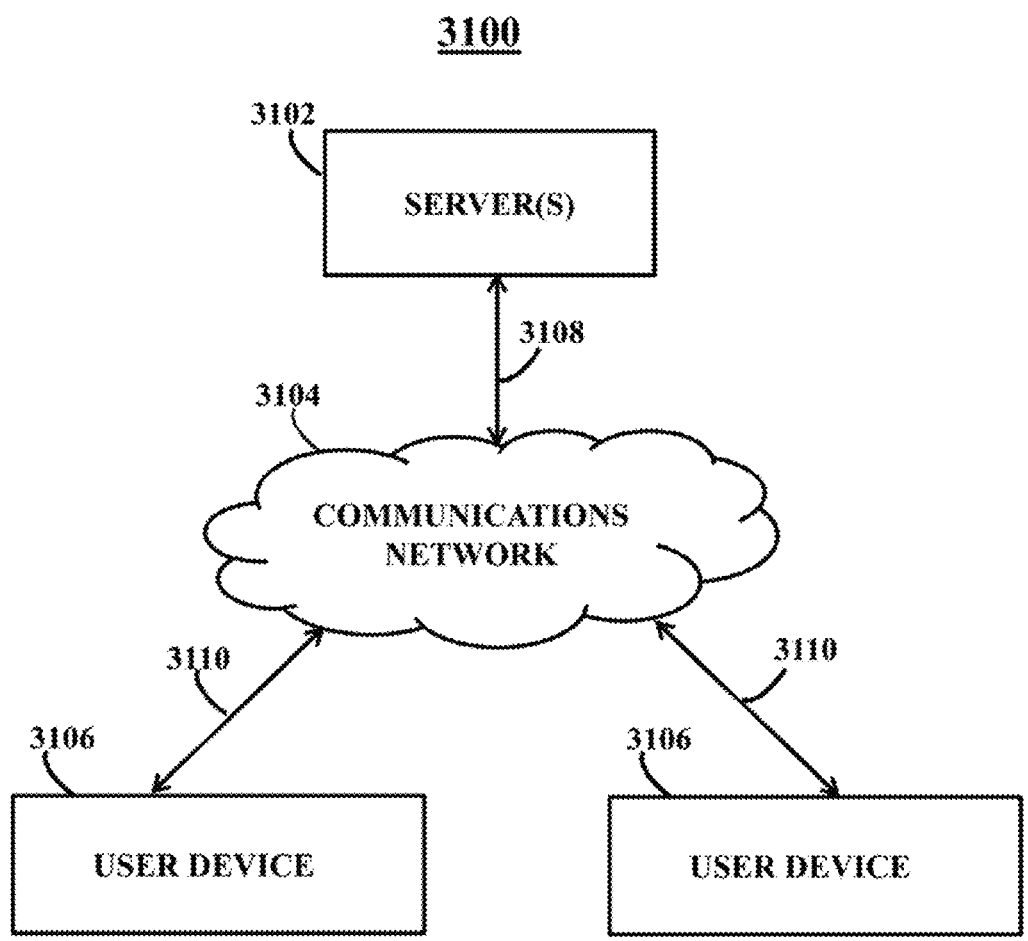
FIG. 31 shows a generalized block diagram of an example of a system for logging phone calls in accordance with some embodiments of the disclosed subject matter.

Turning to FIG. 31, a generalized block diagram of an example 3100 of a system for logging phone calls in accordance with some implementations of the disclosed subject matter is shown. As illustrated, system 3100 can include one or more servers 3102, a communications network 3104, one or more user devices 3106, and communication links 3108 and 3110. In some embodiments, one or more of the interfaces illustrated in FIGS. 1-30 and FIGS. 32-48 can be implemented by server(s) 3102 and/or user devices 3106.

Server(s) 3102 can be any suitable server for performing one or more portions of the mechanisms for logging phone calls as illustrated in FIGS. 1-30 and FIGS. 32-48 and/or for performing any other suitable function. Server(s) 3102 can include and/or be any of a general purpose device such as a computer or a special purpose device such as a client, a server, etc. Any of these general or special purpose devices can include any suitable components, such as a hardware processor (which can be a microprocessor, a digital signal process, a controller, etc.), memory, communication interfaces, display controllers, input devices, etc.

User devices 3106 can include a mobile phone, a tablet computer, a laptop computer, a desktop computer, a personal data assistant (PDA), a portable email device, a gaming device, and/or any other suitable device.

Although two user devices 3106 are shown in FIG. 31 to avoid over-complicating the drawing, any suitable number of these devices, and suitable types of these devices, can be used in some implementations.

Each of server(s) 3102 and user devices 3106 can include and/or be any of a general purpose device such as a computer or a special purpose device such as a client, a server, etc. Any of these general or special purpose devices can include any suitable components such as a hardware processor (which can be a microprocessor, digital signal processor, a controller, etc.), memory, communication interfaces, display controllers, input devices, etc.

Moreover, each of server(s) 3102 and user devices 3106 can comprise a storage device, which can include a hard drive, a solid state storage device, a removable storage device, and/or any other suitable storage device. Server(s) 3102 and user devices 3106 can be located at any suitable location. Each of server(s) 3102 and user devices 3106 can be implemented as a stand-alone device or integrated with other components of system 3100.

Communications network 3104 can be any suitable computer network such as the Internet, an intranet, a wide-area network ("WAN"), a local-area network ("LAN"), a wireless network, a digital subscriber line ("DSL") network, a frame relay network, an asynchronous transfer mode ("ATM") network, a virtual private network ("VPN"), a satellite network, a mobile phone network, a mobile data network, a cable network, a telephone network, a fiber optic network, and/or any other suitable communication network, or any combination of any of such networks.

Server(s) 3102 and user device 3106 can be connected to communications network 3104 through communication links 3108 and 3110, respectively. Communication links 3108 and 3110 can be any suitable communication links, such as network links, dial-up links, wireless links, hard-wired links, any other suitable communication links, or a combination of such links.

In some implementations, any suitable computer readable media can be used for storing instructions for performing the processes described herein. For example, in some implementations, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Accordingly, methods, systems, and media for logging phone calls are provided.

The provision of the examples described herein (as well as clauses phrased as "such as," "e.g.," "including," and the like) should not be interpreted as limiting the disclosed subject matter to the specific examples; rather, the examples are intended to illustrate only some of many possible aspects.

Although the disclosed subject matter has been described and illustrated in the foregoing illustrative implementations, it is understood that the present disclosure has been made only by way of example, and that numerous changes in the details of implementation of the disclosed subject matter can be made without departing from the spirit and scope of the disclosed subject matter. Features of the disclosed implementations can be combined and rearranged in various ways.

What is claimed is:

1. A method for logging phone calls, the method comprising:
    receiving a user request to make a phone call to a client;
    receiving, from a first server, contact information associated with the client;
    causing the phone call to be made based on the received contact information;
    receiving a user input of content relating to the phone call;
    creating at least one note based on the received user input;
    in response to determining that the phone call has been terminated, transmitting information about the phone call and the created note to the first server;
    causing the information about the phone call and the note to be stored in association with the client by the first server;
    causing the information about the phone call and the note to be transmitted from the first server to a second server, wherein the information and the note are stored in an electronic medical record on the second server that is associated with the client;
    receiving a user request for analytical information relating to the client;
    receiving, from the first server, an analysis of a plurality of phone calls associated with the client over a period of time, wherein the analysis is based at least in part on a total duration of the plurality of phone calls during the period of time and a plurality of notes associated with the plurality of phone calls;
    causing the analytical information to be presented based on the received analysis;
    generating an audio recording based on the received user input;
    generating encrypted data by encrypting the audio recording and the information about the phone call;
    transmitting the encrypted data to the first server; and
    causing the encrypted data to be stored in association with the electronic medical record associated with the client, wherein the first server and the second server are compliant with Health Insurance Portability and Accountability Act (HIPAA) regulations.

2. The method of claim 1, further comprising:
    receiving an indication that the analytical information is to be exported in a predetermined format;
    causing the analytical information to be exported in the predetermined format; and
    causing the exported analytical information to be stored in association with the electronic medical record associated with the client.

3. The method of claim 1, further comprising:
    receiving a user selection of at least a portion of the presented analytical information;
    identifying at least one of the plurality of phone calls based on the user selection;
    receiving an indication that the identified phone call is billable;
    determining a billing rate for the selected phone call in response to receiving the indication;
    calculating a charge for the phone call based on the billing rate; and
    causing an invoice to be generated for the client based on the charge.

4. The method of claim 1, wherein the information about the phone call comprises at least one of a duration of the phone call, a date of the phone call, and a date related to a follow up phone call to the client.

5. A method for logging phone calls, the method comprising:
    receiving a user request to make a phone call to a client;
    receiving, from a first server, contact information associated with the client;
    causing the phone call to be made based on the received contact information;
    receiving a user input of content relating to the phone call;
    creating at least one note based on the received user input;
    in response to determining that the phone call has been terminated, transmitting information about the phone call and the created note to the first server;
    causing the information about the phone call and the note to be stored in association with the client by the first server;
    causing the information about the phone call and the note to be transmitted from the first server to a second server, wherein the information and the note are stored in an electronic medical record on the second server that is associated with the client;
    receiving a user request for analytical information relating to the client;
    receiving, from the first server, an analysis of a plurality of phone calls associated with the client over a period of time, wherein the analysis is based at least in part on a total duration of the plurality of phone calls during the period of time and a plurality of notes associated with the plurality of phone calls;
    causing the analytical information to be presented based on the received analysis;
    receiving an indication that the phone call is to be automatically recorded;
    recording audio associated with the phone call;
    transmitting the recorded audio to the first server; and
    causing the recorded audio to be stored in association with the electronic medical record associated with the client, wherein the first server and the second server are compliant with Health Insurance Portability and Accountability Act (HIPAA) regulations.

6. The method of claim 5, further comprising:
receiving an indication that the analytical information is to be exported in a predetermined format;
causing the analytical information to be exported in the predetermined format; and
causing the exported analytical information to be stored in association with the electronic medical record associated with the client.

7. The method of claim 5, further comprising:
receiving a user selection of at least a portion of the presented analytical information;
identifying at least one of the plurality of phone calls based on the user selection;
receiving an indication that the identified phone call is billable;
determining a billing rate for the selected phone call in response to receiving the indication;
calculating a charge for the phone call based on the billing rate; and
causing an invoice to be generated for the client based on the charge.

8. A system for logging phone calls, the system comprising:
a hardware processor that is configured to:
receive a user request to make a phone call to a client;
receive, from a first server, contact information associated with the client;
cause the phone call to be made based on the received contact information;
receive a user input of content relating to the phone call;
create at least one note based on the received user input;
in response to determining that the phone call has been terminated, transmit information about the phone call and the created note to the first server;
cause the information about the phone call and the note to be stored in association with the client by the first server;
cause the information about the phone call and the note to be transmitted from the first server to a second server, wherein the information and the note are stored in an electronic medical record on the second server that is associated with the client;
receive a user request for analytical information relating to the client;
receive, from the first server, an analysis of a plurality of phone calls associated with the client over a period of time, wherein the analysis is based at least in part on a total duration of the plurality of phone calls during the period of time and a plurality of notes associated with the plurality of phone calls;
cause the analytical information to be presented based on the received analysis;
generate an audio recording based on the received user input;
generate encrypted data by encrypting the audio recording and the information about the phone call;
transmit the encrypted data to the first server; and
cause the encrypted data to be stored in association with the electronic medical record associated with the client,
wherein the first server and the second server are compliant with Health Insurance Portability and Accountability Act (HIPAA) regulations.

9. The system of claim 8, wherein the hardware processor is further configured to:
receive an indication that the analytical information is to be exported in a predetermined format;
cause the analytical information to be exported in the predetermined format; and
cause the exported analytical information to be stored in association with the electronic medical record associated with the client.

10. The system of claim 8, wherein the hardware processor is further configured to:
receive a user selection of at least a portion of the presented analytical information;
identify at least one of the plurality of phone calls based on the user selection;
receive an indication that the identified phone call is billable;
determine a billing rate for the selected phone call in response to receiving the indication;
calculate a charge for the phone call based on the billing rate; and
cause an invoice to be generated for the client based on the charge.

11. The system of claim 8, wherein the information about the phone call comprises at least one of a duration of the phone call, a date of the phone call, and a date related to a follow up phone call to the client.

12. A system for logging phone calls, the system comprising:
a hardware processor that is configured to:
receive a user request to make a phone call to a client;
receive, from a first server, contact information associated with the client;
cause the phone call to be made based on the received contact information;
receive a user input of content relating to the phone call;
create at least one note based on the received user input;
in response to determining that the phone call has been terminated, transmit information about the phone call and the created note to the first server;
cause the information about the phone call and the note to be stored in association with the client by the first server;
cause the information about the phone call and the note to be transmitted from the first server to a second server, wherein the information and the note are stored in an electronic medical record on the second server that is associated with the client;
receive a user request for analytical information relating to the client;
receive, from the first server, an analysis of a plurality of phone calls associated with the client over a period of time, wherein the analysis is based at least in part on a total duration of the plurality of phone calls during the period of time and a plurality of notes associated with the plurality of phone calls;
cause the analytical information to be presented based on the received analysis;
receive an indication that the phone call is to be automatically recorded;
record audio associated with the phone call;
transmit the recorded audio to the first server; and
cause the recorded audio to be stored in association with the electronic medical record associated with the client,
wherein the first server and the second server are compliant with Health Insurance Portability and Accountability Act (HIPAA) regulations.

13. The system of claim 12, wherein the hardware processor is further configured to:

receive an indication that the analytical information is to be exported in a predetermined format;

cause the analytical information to be exported in the predetermined format; and cause the exported analytical information to be stored in association with the electronic medical record associated with the client.

14. The system of claim 12, wherein the hardware processor is further configured to:

receive a user selection of at least a portion of the presented analytical information;

identify at least one of the plurality of phone calls based on the user selection;

receive an indication that the identified phone call is billable;

determine a billing rate for the selected phone call in response to receiving the indication;

calculate a charge for the phone call based on the billing rate; and cause an invoice to be generated for the client based on the charge.

15. A non-transitory computer-readable medium containing computer executable instructions that, when executed by a processor, cause the processor to perform a method for logging phone calls, the method comprising:

receiving a user request to make a phone call to a client;

receiving, from a first server, contact information associated with the client;

causing the phone call to be made based on the received contact information;

receiving a user input of content relating to the phone call;

creating at least one note based on the received user input;

in response to determining that the phone call has been terminated, transmitting information about the phone call and the created note to the first server;

causing the information about the phone call and the note to be stored in association with the client by the first server;

causing the information about the phone call and the note to be transmitted from the first server to a second server, wherein the information and the note are stored in an electronic medical record on the second server that is associated with the client;

receiving a user request for analytical information relating to the client;

receiving, from the first server, an analysis of a plurality of phone calls associated with the client over a period of time, wherein the analysis is based at least in part on a total duration of the plurality of phone calls during the period of time and a plurality of notes associated with the plurality of phone calls;

causing the analytical information to be presented based on the received analysis;

generating an audio recording based on the received user input;

generating encrypted data by encrypting the audio recording and the information about the phone call;

transmitting the encrypted data to the first server; and causing the encrypted data to be stored in association with the electronic medical record associated with the client, wherein the first server and the second server are compliant with Health Insurance Portability and Accountability Act (HIPAA) regulations.

16. The non-transitory computer-readable medium of claim 15, wherein the method further comprises:

receiving an indication that the analytical information is to be exported in a predetermined format;

causing the analytical information to be exported in the predetermined format; and causing the exported analytical information to be stored in association with the electronic medical record associated with the client.

17. The non-transitory computer-readable medium of claim 15, wherein the method further comprises:

receiving a user selection of at least a portion of the presented analytical information;

identifying at least one of the plurality of phone calls based on the user selection;

receiving an indication that the identified phone call is billable;

determining a billing rate for the selected phone call in response to receiving the indication;

calculating a charge for the phone call based on the billing rate; and causing an invoice to be generated for the client based on the charge.

18. The non-transitory computer-readable medium of claim 15, wherein the information about the phone call comprises at least one of a duration of the phone call, a date of the phone call, and a date related to a follow up phone call to the client.

19. A non-transitory computer-readable medium containing computer executable instructions that, when executed by a processor, cause the processor to perform a method for logging phone calls, the method comprising:

receiving a user request to make a phone call to a client;

receiving, from a first server, contact information associated with the client;

causing the phone call to be made based on the received contact information;

receiving a user input of content relating to the phone call;

creating at least one note based on the received user input;

in response to determining that the phone call has been terminated, transmitting information about the phone call and the created note to the first server;

causing the information about the phone call and the note to be stored in association with the client by the first server;

causing the information about the phone call and the note to be transmitted from the first server to a second server, wherein the information and the note are stored in an electronic medical record on the second server that is associated with the client;

receiving a user request for analytical information relating to the client receiving, from the first server, an analysis of a plurality of phone calls associated with the client over a period of time, wherein the analysis is based at least in part on a total duration of the plurality of phone calls during the period of time and a plurality of notes associated with the plurality of phone calls;

causing the analytical information to be presented based on the received analysis;

receiving an indication that the phone call is to be automatically recorded;

recording audio associated with the phone call;

transmitting the recorded audio to the first server; and causing the recorded audio to be stored in association with the electronic medical record associated with the client, wherein the first server and the second server are compliant with Health Insurance Portability and Accountability Act (HIPAA) regulations.

20. The non-transitory computer-readable medium of claim 19, wherein the method further comprises:

receiving an indication that the analytical information is to be exported in a predetermined format;

causing the analytical information to be exported in the predetermined format; and causing the exported analytical information to be stored in association with the electronic medical record associated with the client.

21. The non-transitory computer-readable medium of claim 19, wherein the method further comprises:

receiving a user selection of at least a portion of the presented analytical information;

identifying at least one of the plurality of phone calls based on the user selection;

receiving an indication that the identified phone call is billable;

determining a billing rate for the selected phone call in response to receiving the indication;

calculating a charge for the phone call based on the billing rate; and causing an invoice to be generated for the client based on the charge.

\* \* \* \* \*